(12) United States Patent (10) Patent No.: US 8,415,059 B2
Minteer et al. (45) Date of Patent: Apr. 9, 2013

(54) DIRECT ELECTRON TRANSFER USING ENZYMES IN BIOANODES, BIOCATHODES, AND BIOFUEL CELLS

(75) Inventors: Shelley D. Minteer, Pacific, MO (US); Becky L. Treu, St. Peters, MO (US); Rodica Duma, St. Louis, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 12/092,118

(22) PCT Filed: Nov. 2, 2006

(86) PCT No.: PCT/US2006/060492
§ 371 (c)(1),
(2), (4) Date: Sep. 30, 2008

(87) PCT Pub. No.: WO2007/084249
PCT Pub. Date: Jul. 26, 2007

(65) Prior Publication Data
US 2011/0014549 A9 Jan. 20, 2011

Related U.S. Application Data

(60) Provisional application No. 60/732,742, filed on Nov. 2, 2005, provisional application No. 60/784,650, filed on Mar. 22, 2006.

(51) Int. Cl.
*H01M 8/16* (2006.01)
(52) U.S. Cl.
USPC .......................................................... 429/401
(58) Field of Classification Search ........................ None
See application file for complete search history.

(56) References Cited

U.S. PATENT DOCUMENTS

| 4,117,202 A | 9/1978 | Beck |
| 4,207,076 A | 6/1980 | Bove et al. |
| 4,224,125 A | 9/1980 | Nakamura et al. |

(Continued)

FOREIGN PATENT DOCUMENTS

| EP | 0 300 082 A2 | 1/1989 |
| EP | 0 667 397 A1 | 8/1995 |

(Continued)

OTHER PUBLICATIONS

Huang, H., et al., "Electrochemistry and Electrocatalysis with Heme Proteins in Chitosan Biopolymer Films," Analytical Biochemistry, 2002, pp. 141-151, vol. 308.

(Continued)

*Primary Examiner* — Patrick Ryan
*Assistant Examiner* — Wyatt McConnell
(74) *Attorney, Agent, or Firm* — Senniger Powers LLP

(57) ABSTRACT

Bioanodes, biocathodes, and biofuel cells comprising an electron conductor, at least one anode enzyme or cathode enzyme, and an enzyme immobilization material. The anode enzyme is capable of reacting with a fuel fluid to produce an oxidized form of the fuel fluid, and capable of releasing electrons to the electron conductor. The cathode enzyme is capable of reacting with an oxidant to produce water, and capable of gaining electrons from the electron conductor. The enzyme immobilization material for both the anode enzyme and the cathode enzyme is capable of immobilizing and stabilizing the enzyme, and is permeable to the fuel fluid and/or the oxidant.

29 Claims, 11 Drawing Sheets

U.S. PATENT DOCUMENTS

| | | | |
|---|---|---|---|
| 4,490,464 A | 12/1984 | Gorton et al. | |
| 4,705,503 A | 11/1987 | Dorman et al. | |
| 4,761,209 A | 8/1988 | Bonaventura et al. | |
| 4,970,145 A * | 11/1990 | Bennetto et al. | 204/403.11 |
| 5,211,984 A | 5/1993 | Wilson | |
| 5,262,035 A | 11/1993 | Gregg et al. | |
| 5,262,305 A | 11/1993 | Heller et al. | |
| 5,264,092 A | 11/1993 | Skotheim et al. | |
| 5,264,105 A | 11/1993 | Gregg et al. | |
| 5,320,725 A | 6/1994 | Gregg et al. | |
| 5,356,786 A | 10/1994 | Heller et al. | |
| 5,393,615 A | 2/1995 | Corey et al. | |
| 5,521,101 A | 5/1996 | Saini et al. | |
| 5,593,852 A | 1/1997 | Heller et al. | |
| 5,665,222 A | 9/1997 | Heller et al. | |
| 5,718,947 A | 2/1998 | Martin et al. | |
| 5,820,551 A | 10/1998 | Hill et al. | |
| 5,919,583 A | 7/1999 | Grot et al. | |
| 6,294,281 B1 | 9/2001 | Heller | |
| 6,294,291 B1 | 9/2001 | Ozaki et al. | |
| 6,387,625 B1 | 5/2002 | Eckhardt et al. | |
| 6,460,733 B2 | 10/2002 | Acker et al. | |
| 6,500,571 B2 | 12/2002 | Liberatore et al. | |
| 6,531,239 B2 | 3/2003 | Heller | |
| 7,368,190 B2 * | 5/2008 | Heller et al. | 429/2 |
| 2002/0025456 A1 | 2/2002 | Gieshoff et al. | |
| 2002/0025469 A1 | 2/2002 | Heller | |
| 2002/0122972 A1 | 9/2002 | Klitsner et al. | |
| 2002/0127440 A1 | 9/2002 | Yamamoto et al. | |
| 2003/0027023 A1 | 2/2003 | Dutil et al. | |
| 2003/0039868 A1 | 2/2003 | Liberatore et al. | |
| 2003/0087144 A1 | 5/2003 | Sun et al. | |
| 2003/0148169 A1 | 8/2003 | Willner et al. | |
| 2003/0164335 A1 | 9/2003 | Grate et al. | |
| 2003/0198858 A1 | 10/2003 | Sun et al. | |
| 2004/0101741 A1 * | 5/2004 | Minteer et al. | 429/43 |
| 2004/0121018 A1 | 6/2004 | Grate et al. | |
| 2004/0214053 A1 | 10/2004 | Armstrong | |
| 2004/0217016 A1 | 11/2004 | Khan | |
| 2005/0095466 A1 | 5/2005 | Minteer et al. | |
| 2005/0101841 A9 | 5/2005 | Kaylor et al. | |

FOREIGN PATENT DOCUMENTS

| | | |
|---|---|---|
| EP | 0 747 984 A2 | 12/1996 |
| WO | 00/22688 A3 | 4/2000 |
| WO | 03/006713 A1 | 1/2003 |
| WO | 03/019170 A1 | 3/2003 |
| WO | 03/019705 A2 | 3/2003 |
| WO | 03/067697 A2 | 8/2003 |
| WO | 03/106966 A2 | 12/2003 |
| WO | 2004/079848 A2 | 9/2004 |
| WO | 2005/096430 A1 | 10/2005 |

OTHER PUBLICATIONS

Ivnitski, D., et al., "Glucose Oxidase Anode for Biofuel Cell Based on Direct Electron Transfer," Electrochemistry Communications, 2006, pp. 1204-1210, vol. 8.

Klotzbach, T., et al., "Effects of Hydrophobic Modification of Chitosan and Nafion on Transport Properties, Ion-Exchange Capacities, and Enzyme Immobilization," Journal of Membrane Science, 2006, pp. 276-283, vol. 282.

Krajewska, B., "Application of Chitin- and Chitosan-Based Materials for Enzyme Immobilizations: A Review," Enzyme and Microbial Technology, 2004, pp. 126-139, vol. 35.

Liu, C.-G., et al., "Self-Assembled Nanoparticles Based on Linoleic-Acid Modified Chitosan: Stability and Absorption of Trypsin," Carbohydrate Polymers, 2005, pp. 293-298, vol. 62.

Supplementary European Search Report for counterpart foreign Application No. EP06846213 dated Oct. 26, 2009, 3 pages.

Supplementary European Search Report for counterpart foreign Application No. EP06849336 dated Oct. 12, 2009, 3 pages.

Advanced Enzymes "Glucose Oxidase, Enzyme, Glucose Oxidase Test, Glucose Oxidase Reaction, Glucose Oxidase Method, Glucose Oxidase Assay" accessed Mar. 12, 2008 at http://www.enzymeindia.com/enzymes/glucose-oxidase.asp.

"Alcohol Dehydrogenase" Worthington Enzyme Manual, accessed Nov. 14, 2003 at http://www.worthington-biochem.com/ADH/default.html.

Blaedel, W. J., et al., "Study of the Electrochemical Oxidation of Reduced Nicotinamide Adenine Dinucleotide," Analytical Chemistry, Jul. 1975, pp. 1337-1343, vol. 47, No. 8.

Chen, T., et al., "A Miniature Biofuel Cell," Journal of the American Chemical Society, 2001, pp. 8630-8631, vol. 123, No. 35.

Davis, G., et al., "Bioelectrochemical Fuel Cell and Sensor Based on a Quinoprotein, Alcohol Dehydrogenase," Enzyme Microbial Technology, Sep. 1983, pp. 383-388, vol. 5.

Frébortová, J., et al., "Intramolecular Electron Transport in Quinoprotein Alcohol Dehydrogenase of Acetobacter Methanolicus: A Redox-Titration Study," Biochemica et Biophysica Acta, 1998, pp. 24-34, vol. 1363.

Glucose Oxidase Pathway accessed on Mar. 12, 2008 at http://www.biochemj.org/bj/347/0553/bj3470553f03.gif.

Green, D. W., et al., "Inversion of the Substrate Specificity of Yeast Alcohol Dehydrogenase," The Journal of Biological Chemistry, 1993, pp. 7792-7798, vol. 268, No. 11.

Jin, L., et al., "A Study of Uricase Biosensor Based on a Glassy Carbon Electrode Modified with Nafion and Methyl Viologen," Mikrochimica Acta, 1993, pp. 71-75, vol. 112.

Karyakin, A. A., et al., "Improvement of Electrochemical Biosensors Using Enzyme Immobilization from Water-Organic Mixtures with a High Content of Organic Solvent," Analytical Chemistry, Dec. 15, 1996, pp. 4335-4341, vol. 68, No. 24.

Kim, H. H., et al., "A Miniature Membrane-less Biofuel Cell Operating Under Physiological Conditions at 0.5 V," Journal of the Electrochemical Society, 2003, pp. A209-A213, vol. 150, No. 2.

Leonida, M. D., et al., "Co-Electropolymerization of a Viologen Oligomer and Lipoamide Dehydrogenase on an Electrode Surface. Application to Cofactor Regeneration," Bioorganic & Medicinal Chemistry Letters, 1996, pp. 1663-1666, vol. 6, No. 14.

Ohara, T. J., et al., "Wired" Enzyme Electrodes for Amperometric Determination of Glucose or Lactate in the Presence of Interfering Substances, Analytical Chemistry, Aug. 1, 1994, pp. 2451-2457, vol. 66, No. 15.

Palmore, G. T. R., et al., "A Methanol\Dioxygen Biofuel Cell That Uses NAD+-Dependent Dehydrogenases as Catalysts: Application of an Electro-Enzymatic Method to Regenerate Nicotinamide Adenine Dinucleotide at Low Overpotentials," Journal of Electroanalytical Chemistry, 1998, pp. 155-161, vol. 443.

Plotkin, E. V., et al., "Methanol Dehydrogenase Bioelectrochemical Cell and Alcohol Detector," Biotechnology Letters, 1981, pp. 187-192, vol. 3, No. 4.

Schrenk, M. J., et al., "Effect of Mixture Casting Nafion® with Quaternary Ammonium Bromide Salts on the Ion-Exchange Capacity and Mass Transport in the Membranes," Journal of Membrane Science, 2002, pp. 3-10, vol. 205.

Tayhas, G., et al., "Microbial and Enzymatic Biofuel Cells," in ACS Symposium Series 566, 1994, pp. 271-290.

Thomas, T. J., et al., "Effects of Annealing on Mixture-Cast Membranes of Nafion® and Quaternary Ammonium Bromide Salts," Journal of Membrane Science, 2003, pp. 55-66, vol. 213.

Yamada, Y., et al., "Effective Bioconversion with Continuous Product Recovery Using AOT/Lecithin Mixed Reverse Micellar Systems and Centrifugal Partition Chromatography as a Novel Bioreactor," Biotechnol. Prog., 1995, pp. 682-688, vol. 11, No. 6.

Yoshioka, H., et al., "Chitosan-Derived Polymer-Surfactants and Their Micellar Properties," Abstract, Biosci. Biotechnol. Biochem., Oct. 1995, pp. 1901-1904, vol. 59, No. 10.

Yue, P. L., et al., "Enzymatic Oxidation of C1 Compounds in a Biochemical Fuel Cell," Chemical Engineering Journal, 1986, pp. B69-B77, vol. 33.

Zawodzinski, T. A., et al., "Thin-Layer Composite Enzyme Electrodes for Glucose Determinations," Electroanalysis, 1995, pp. 1035-1040, vol. 7, No. 11.

Zhou, D., et al., "The Electrochemical Polymerization of Methylene Green and its Electrocatalysis for the Oxidation of NADH," Analytica Chimica Acta, 1996, pp. 41-48, vol. 329.

Buttry, D. A., et al., "Electrochemical Control of the Luminescent Lifetime of Ru(bpy)32+* Incorporated in Nafion Films on Graphite Electrodes," Journal of the American Chemical Society, 1982, pp. 4824-4829, vol. 104, No. 18.

Durán, N., et al., "Applications of Laccases and Tyrosinases (Phenoloxidases) Immobilized on Different Supports: A Review," Enzyme and Microbial Technology, 2002, pp. 907-931, vol. 31.

Fernández-Sánchez, C., et al., "Voltammetric Monitoring of Laccase-catalysed Mediated Reactions," Bioelectrochemistry, 2002, pp. 149-156, vol. 58.

Guillén, F., et al., "Oxygen Activation During Oxidation of Methoxyhydroquinones by Laccase from *Pleurotus eryngii*," Applied and Environmental Microbiology, Jan. 2000, pp. 170-175, vol. 66, No. 1.

Mano, N., et al., "An Oxygen Cathode Operating in a Physiological Solution," Journal of the American Chemical Society, 2002, pp. 6480-6486, vol. 124, No. 22.

Trudeau, F., et al., "Reagentless Mediated Laccase Electrode for the Detection of Enzyme Modulators," Analytical Chemistry, Mar. 1, 1997, pp. 882-886, vol. 69, No. 5.

Zhang, C., et al., "Evaluation of Substituted-1,10-phenanthroline Complexes of Osmium as Mediator for Glucose Oxidase of *Aspergillus niger*," Analytica Chimica Acta, 2000, pp. 225-232, vol. 408.

* cited by examiner

DIRECT ELECTRON TRANSFER USING ENZYMES IN BIOANODES, BIOCATHODES, AND BIOFUEL CELLS This invention was made with Government support under Grant No. 3-00475 awarded by the Office of Navel Research, Grant No. 3-00487 awarded by the Defense Advanced Research Projects Agency, and Grant No. 300477 awarded by the U.S. Central Intelligence Agency. The Government has certain rights in the invention.

BACKGROUND OF THE INVENTION

The present invention is directed in general to biological enzyme-based fuel cells (a.k.a. biofuel cells) and their methods of manufacture and use. More specifically, the invention is directed to bioanodes, biocathodes, and biofuel cells comprising enzymes capable of direct electron transfer between the fuel fluid and electron conductor, and their method of manufacture and use.

A biofuel cell is an electrochemical device in which energy derived from chemical reactions is converted to electrical energy by means of the catalytic activity of living cells and/or their enzymes. Biofuel cells generally use complex molecules to generate at the anode the hydrogen ions required to reduce oxygen to water, while generating free electrons for use in electrical applications. A bioanode is the electrode of the biofuel cell where electrons are released upon the oxidation of a fuel and a biocathode is the electrode where electrons and protons from the anode are used by the catalyst to reduce peroxide or oxygen to water. Biofuel cells differ from the traditional fuel cell by the material used to catalyze the electrochemical reaction. Rather than using precious metals as catalysts, biofuel cells rely on biological molecules such as enzymes to carry out the reaction.

Most bioanodes and biocathodes include electron mediators. But, some bioanodes and biocathodes including electron mediators may have reduced lifetimes, reduced stability, unfavorable thermodynamics, and low activity of the electron mediator. Thus, a need exists for bioanodes and biocathodes that do not have the problems associated with inclusion of electron mediators.

SUMMARY OF THE INVENTION

Among the various aspects of the present invention is a bioanode comprising an electron conductor; at least one anode enzyme; and an enzyme immobilization material. The anode enzyme is capable of reacting with a fuel fluid to produce an oxidized form of the fuel fluid, and capable of releasing electrons to the electron conductor. The enzyme immobilization material is capable of immobilizing and stabilizing the enzyme, and is permeable to the fuel fluid.

Another aspect is a biocathode comprising an electron conductor; at least one cathode enzyme; and an enzyme immobilization material. The cathode enzyme is capable of reacting with an oxidant to produce water, and capable of gaining electrons from the electron conductor. The enzyme immobilization material is capable of immobilizing and stabilizing the enzyme, and is permeable to the oxidant.

Yet another aspect is a biofuel cell comprising a fuel fluid, a bioanode as described above, and a biocathode as described above. A further aspect is a biofuel cell comprising a fuel fluid, a bioanode as described above, and a cathode. Also, another aspect is biofuel cell comprising a fuel fluid, an anode, and a biocathode as described above.

A method of generating electricity using the biofuel cells described herein comprising oxidizing the fuel fluid at the anode or bioanode and reducing the oxidant at the cathode or biocathode.

DETAILED DESCRIPTION OF THE INVENTION

Figure 1A:
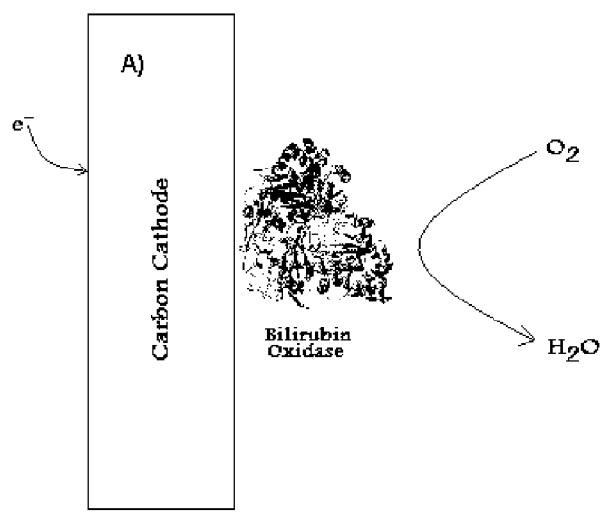
FIG. 1A shows the chemistry occurring at a direct electron transfer-based bilirubin oxidase biocathode and FIG. 1B shows the chemistry occurring at a biocathode including electron mediators.
Figure 1B:
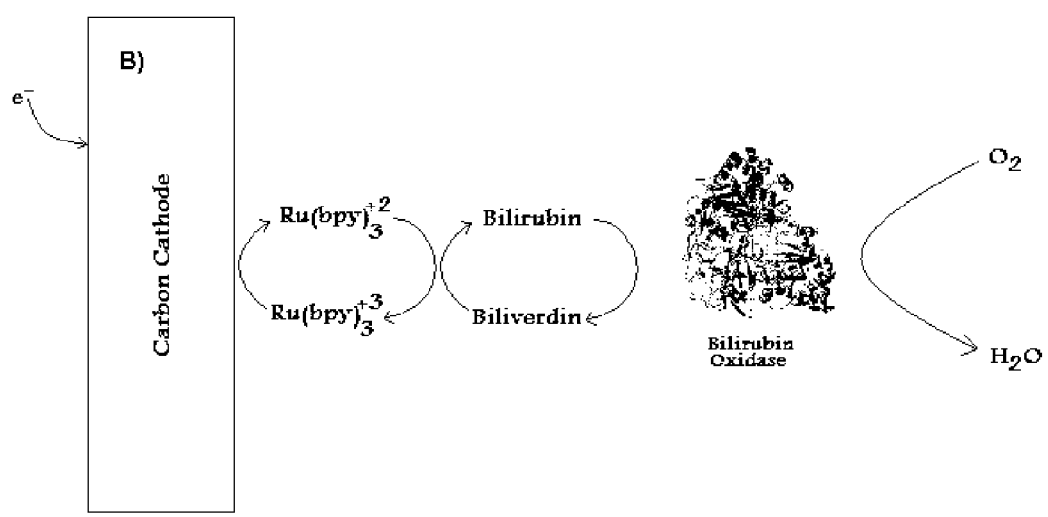

The present invention is directed to bioanodes, biocathodes, and biofuel cells comprising an enzyme capable of direct electron transfer with the electron conductor. Stated another way, the bioanode, and a biofuel cell including such bioanode, contain an anode enzyme capable of releasing electrons to the electron conductor and the biocathode, and a biofuel cell including such biocathode, contain a cathode enzyme capable of gaining electrons from the electron conductor. This capability of electron transfer between the enzyme and the electron conductor is a significant advantage over less efficient electron mediated systems in which the electron mediator must be transported to the vicinity of the redox reaction and may not have the correct local concentration to facilitate a highly efficient redox reaction. By eliminating electron mediators in the system, the reaction kinetics are not limited by mass transport of the electron mediator(s), and thus, can be more efficient. Further, when the enzyme is immobilized on the electron conductor, the redox reaction kinetics can be maximized by having the reactants (enzyme and fuel fluid) in close proximity to the electron conductor, which can then collect the electrons produced.

In yet a further embodiment, the bioelectrode assembly of the present invention has increased enzyme stability. For use in a biocathode or a bioanode, the immobilization material forms a barrier that provides mechanical and chemical stability. Thus, the enzyme is stabilized for a longer period than previously known. For purposes of the present invention, an enzyme is "stabilized" if it retains at least about 75% of its initial catalytic activity upon continuous operation in a biofuel cell for at least about 7 days to about 730 days.

I. Biofuel Cell

Among the various aspects of the invention is a biofuel cell utilizing a fuel fluid to produce electricity via enzyme mediated redox reactions taking place at electrodes with immobilized enzymes therein. As in a standard electrochemical cell, the anode is the site for an oxidation reaction of a fuel fluid with a concurrent release of electrons. The electrons are directed from the anode through an electrical connector to some power consuming device. The electrons move through the device to another electrical connector, which transports the electrons to the biofuel cell's biocathode where the electrons are used to reduce an oxidant to produce water. In this manner, the biofuel cell of the present invention acts as an energy source (electricity) for an electrical load external thereto. To facilitate the fuel fluid's redox reactions, the electrodes comprise an electron conductor, an enzyme, and an enzyme immobilization material.

At the biocathode, electrons originating from the bioanode flow into the biocathode's electron conductor. There, the electrons contact a cathode enzyme capable of gaining electrons from the electron conductor. In various embodiments, an enzyme immobilization material permeable to the oxidant is present, and which is capable of immobilizing and stabilizing the enzyme.

The biofuel cell of the present invention comprises a biocathode and/or a bioanode. Generally, the bioanode comprises elements that effect the oxidation of fuel fluid whereby electrons are released and directed to an external electrical load. The resulting electrical current powers the electrical load, with electrons being subsequently directed to a biocathode where an oxidant is reduced and water is produced.

A. Biocathode

The biocathode in accordance with this invention comprises an electron conductor, and an enzyme which is immobilized in an enzyme immobilization material. In one embodiment, these components are adjacent to one another, meaning they are physically or chemically connected by appropriate means.

1. Electron Conductor

The electron conductor is a substance that conducts electrons. The electron conductor can be organic or inorganic in nature as long as it is able to conduct electrons through the material. The electron conductor can be a carbon-based material, stainless steel, stainless steel mesh, a metallic conductor, a semiconductor, a metal oxide, or a modified conductor. In preferred embodiments, the electron conductor is a carbon-based material.

Particularly suitable electron conductors are carbon-based materials. Exemplary carbon-based materials are carbon cloth, carbon paper, carbon screen printed electrodes, carbon paper (Toray), carbon paper (ELAT), carbon black (Vulcan XC-72, E-tek), carbon black, carbon powder, carbon fiber, single-walled carbon nanotubes, double-walled carbon nanotubes, multi-walled carbon nanotubes, carbon nanotubes arrays, diamond-coated conductors, glassy carbon and mesoporous carbon. In addition, other exemplary carbon-based materials are graphite, uncompressed graphite worms, delaminated purified flake graphite (Superior® graphite), high performance graphite and carbon powders (Formula BT™, Superior® graphite), highly ordered pyrolytic graphite, pyrolytic graphite and polycrystalline graphite. A preferred electron conductor (support membrane) is a sheet of carbon cloth.

In a further embodiment, the electron conductor can be made of a metallic conductor. Suitable electron conductors can be prepared from gold, platinum, iron, nickel, copper, silver, stainless steel, mercury, tungsten, and other metals suitable for electrode construction. In addition, electron conductors which are metallic conductors can be constructed of nanoparticles made of cobalt, carbon, and other suitable metals. Other metallic electron conductors can be silver-plated nickel screen printed electrodes.

In addition, the electron conductor can be a semiconductor. Suitable semiconductor materials include silicon and germanium, which can be doped with other elements. The semiconductors can be doped with phosphorus, boron, gallium, arsenic, indium or antimony, or a combination thereof.

Other electron conductors can be metal oxides, metal sulfides, main group compounds (i.e., transition metal compounds), and materials modified with electron conductors. Exemplary electron conductors of this type are nanoporous titanium oxide, tin oxide coated glass, cerium oxide particles, molybdenum sulfide, boron nitride nanotubes, aerogels modified with a conductive material such as carbon, solgels modified with conductive material such as carbon, ruthenium carbon aerogels, and mesoporous silicas modified with a conductive material such as carbon.

In various preferred embodiments, the electron conductor is a carbon cloth, a carbon nanotube, an expanded graphite worm, a carbon paste, and combinations thereof. More preferably, the electron conductor is a carbon nanotube.

2. Enzyme

In accordance with the invention, an enzyme reduces an oxidant at the biocathode. Generally, enzymes containing more than one redox center are useful for the biocathodes and biofuel cells of the invention. For example, bilirubin oxidase contains a four atom copper core with a T1 copper center for accepting electrons from donating substrates and a T2-T3 electron donating cluster to reduce oxygen. Without being bound by theory, it is proposed that many enzymes having more than one redox center can act as their own internal mediator for electron transfer to and from the electron conductor. Exemplary enzymes for use in a biocathode are bilirubin oxidase, laccase, superoxide dismutase, peroxidase, or combinations thereof. In various preferred embodiments, when the oxidant is oxygen, the enzyme is a bilirubin oxidase. In some embodiments, when the oxidant is peroxide, the enzyme is superoxide dismutase.

3. Enzyme Immobilization Material

An enzyme immobilization material is utilized in the biofuel cell at the bioanode and/or the biocathode. In one embodiment, the bioanode's enzyme immobilization material is permeable to the fuel fluid and immobilizes and stabilizes the enzyme. The immobilization material is permeable to the fuel fluid so the oxidation reaction of the fuel at the bioanode can be catalyzed by the immobilized enzyme.

Generally, an enzyme is used to catalyze redox reactions at the biocathode and/or the bioanode. In a bioanode and/or biocathode according to this invention, an enzyme is immobilized in an enzyme immobilization material that both immobilizes and stabilizes the enzyme. Typically, a free enzyme in solution loses its catalytic activity within a few hours to a few days, whereas a properly immobilized and stabilized enzyme can retain its catalytic activity for at least about 7 days to about 730 days. The retention of catalytic activity is defined as the enzyme having at least about 75% of its initial activity, which can be measured by chemiluminescence, electrochemical, UV-Vis, radiochemical, or fluorescence assay. The enzyme retains at least about 75% of its initial activity while the biofuel cell is continually producing electricity for at least about 7 days to about 730 days.

An immobilized enzyme is an enzyme that is physically confined in a certain region of the enzyme immobilization material while retaining its catalytic activity. There are a variety of methods for enzyme immobilization, including carrier-binding, cross-linking and entrapping. Carrier-binding is the binding of enzymes to water-insoluble carriers. Cross-linking is the intermolecular cross-linking of enzymes by bifunctional or multifunctional reagents. Entrapping is incorporating enzymes into the lattices of a semipermeable material. The particular method of enzyme immobilization is not critically important, so long as the enzyme immobilization material (1) immobilizes the enzyme, (2) stabilizes the enzyme, and (3) is permeable to the fuel fluid or oxidant.

With reference to the enzyme immobilization material's permeability to the fuel fluid or oxidant and the immobilization of the enzyme, in various embodiments, the material is permeable to a compound that is smaller than an enzyme. Stated another way, the enzyme immobilization material allows the movement of the fuel fluid or oxidant compound through it so the compound can contact the enzyme. The enzyme immobilization material can be prepared in a manner such that it contains internal pores, channels, openings or a combination thereof, which allow the movement of the compound throughout the enzyme immobilization material, but which constrain the enzyme to substantially the same space within the enzyme immobilization material. Such constraint allows the enzyme to retain its catalytic activity. In various preferred embodiments, the enzyme is confined to a space that is substantially the same size and shape as the enzyme, wherein the enzyme retains substantially all of its catalytic activity. The pores, channels, or openings have physical dimensions that satisfy the above requirements and depend on the size and shape of the specific enzyme to be immobilized.

In various embodiments, the enzyme is preferably located within a pore of the enzyme immobilization material and the compound travels in and out of the enzyme immobilization material through transport channels. The relative size of the pores and transport channels can be such that a pore is large enough to immobilize an enzyme, but the transport channels are too small for the enzyme to travel through them. Further, a transport channel preferably has a diameter of at least about 10 nm. In still another embodiment, the pore diameter to transport channel diameter ratio is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more. In yet another embodiment, preferably, a transport channel has a diameter of at least about 10 nm and the pore diameter to transport channel diameter ratio is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more.

With respect to the stabilization of the enzyme, the enzyme immobilization material provides a chemical and mechanical barrier to prevent or impede enzyme denaturation. To this end, the enzyme immobilization material physically confines the enzyme, preventing the enzyme from unfolding. The process of unfolding an enzyme from a folded three-dimensional structure is one mechanism of enzyme denaturation. In one embodiment, the immobilization material, preferably, stabilizes the enzyme so that the enzyme retains its catalytic activity for at least about 7 days to about 730 days. The retention of catalytic activity is defined by the number of days that the enzyme retains at least about 75% of its initial activity while continually producing electricity as part of a biofuel cell. The enzyme activity can be measured by chemiluminescence, electrochemical, UV-Vis, radiochemical or fluorescence assay wherein the intensity of the property is measured at an initial time. Typically, a fluorescence assay is used to measure the enzyme activity. A free enzyme in solution loses its catalytic activity within hours to a few days. Thus, the immobilization of the enzyme provides a significant advantage in stability. In other embodiments, preferably, the immobilized enzyme retains at least about 75% of its initial catalytic activity for at least about 5, 10, 15, 20, 25, 30, 45, 60, 75, 90, 105, 120, 150, 180, 210, 240, 270, 300, 330, 365, 400, 450, 500, 550, 600, 650, 700, 730 days or more, preferably retaining at least about 80%, 85%, 90%, 95% or more of its initial catalytic activity for at least about 5, 10, 15, 20, 25, 30, 45, 60, 75, 90, 105, 120, 150, 180, 210, 240, 270, 300, 330, 365, 400, 450, 500, 550, 600, 650, 700, 730 days or more.

In some of the embodiments, the enzyme immobilization material has a micellar or inverted micellar structure. Generally, the molecules making up a micelle are amphipathic, meaning they contain a polar, hydrophilic group and a nonpolar, hydrophobic group. The molecules can aggregate to form a micelle, where the polar groups are on the surface of the aggregate and the hydrocarbon, nonpolar groups are sequestered inside the aggregate. Inverted micelles have the opposite orientation of polar groups and nonpolar groups. The amphipathic molecules making up the aggregate can be arranged in a variety of ways so long as the polar groups are in proximity to each other and the nonpolar groups are in proximity to each other. Also, the molecules can form a bilayer with the nonpolar groups pointing toward each other and the polar groups pointing away from each other. Alternatively, a bilayer can form wherein the polar groups can point toward each other in the bilayer, while the nonpolar groups point away from each other.

Certain enzyme immobilization materials, and particularly micellar enzyme immobilization materials and modified-perfluoro sulfonic acid-PTFE copolymers, are described in U.S. patent application Ser. No. 10/931,147 (published as U.S. Patent Application Publication No. 2005/0095466), and U.S. patent application Ser. No. 10/617,452 (published as U.S. Patent Application Publication No. 2004/0101741), both of which are herein incorporated by reference in their entirety.

In one preferred embodiment, the micellar enzyme immobilization material is a modified perfluoro sulfonic acid-PTFE copolymer (or modified perfluorinated ion exchange polymer)(modified Nafion® or modified Flemion®) membrane. The perfluorinated ion exchange polymer membrane is modified with a hydrophobic cation that is larger than the ammonium ($NH_4^+$) ion. The hydrophobic cation serves the dual function of (1) dictating the membrane's pore size and (2) acting as a chemical buffer to help maintain the pore's pH level, both of which stabilize the enzyme.

With regard to the first function of the hydrophobic cation, mixture-casting a perfluoro sulfonic acid-PTFE copolymer (or perfluorinated ion exchange polymer) with a hydrophobic cation to produce a modified perfluoro sulfonic acid-PTFE copolymer (or modified perfluorinated ion exchange polymer)(Nafion® or Flemion®) membrane provides an enzyme immobilization material wherein the pore size is dependent on the size of the hydrophobic cation. Accordingly, the larger the hydrophobic cation, the larger the pore size. This function of the hydrophobic cation allows the pore size to be made larger or smaller to fit a specific enzyme by varying the size of the hydrophobic cation.

Regarding the second function of the hydrophobic cation, the properties of the perfluoro sulfonic acid-PTFE copolymer (or perfluorinated ion exchange polymer) membrane are altered by exchanging the hydrophobic cation for protons as the counterion to the $-SO_3^-$ groups on the perfluoro sulfonic acid-PTFE copolymer (or anions on the perfluorinated ion exchange polymer) membrane. This change in counterion provides a buffering effect on the pH because the hydrophobic cation has a much greater affinity for the $-SO_3^-$ sites than protons do. This buffering effect of the membrane causes the pH of the pore to remain substantially unchanged with changing solution pH; stated another way, the pH of the pore resists changes in the solution's pH. In addition, the membrane provides a mechanical barrier, which further protects the immobilized enzymes. In order to prepare a modified perfluoro sulfonic acid-PTFE copolymer (or perfluorinated ion exchange polymer) membrane, the first step is to cast a suspension of perfluoro sulfonic acid-PTFE copolymer (or perfluorinated ion exchange polymer), particularly Nafion®, with a solution of the hydrophobic cations to form a membrane. The excess hydrophobic cations and their salts are then extracted from the membrane, and the membrane is re-cast. Upon re-casting, the membrane contains the hydrophobic cations in association with the $-SO_3^-$ sites of the perfluoro sulfonic acid-PTFE copolymer (or perfluorinated ion exchange polymer) membrane. Removal of the salts of the hydrophobic cation from the membrane results in a more stable and reproducible membrane since the excess salts can become trapped in the pore or cause voids in the membrane.

In one embodiment, a modified Nafion® membrane is prepared by casting a suspension of Nafion® polymer with a solution of a salt of a hydrophobic cation such as quaternary ammonium bromide. Excess quaternary ammonium bromide or hydrogen bromide are removed from the membrane before it is re-cast to form the salt-extracted membrane. Salt extraction of membranes retains the presence of the quaternary ammonium cations at the sulfonic acid exchange sites, but eliminates complications from excess salt that may be trapped in the pore or may cause voids in the equilibrated membrane. The chemical and physical properties of the salt-extracted membranes have been characterized by voltammetry, ion exchange capacity measurements, and fluorescence microscopy before enzyme immobilization. Exemplary hydrophobic cations are ammonium-based cations, quaternary ammonium cations, alkyltrimethylammonium cations, alkyltriethylammonium cations, organic cations, phosphonium cations, triphenylphosphonium, pyridinium cations, imidazolium cations, hexadecylpyridinium, ethidium, viologens, methyl viologen, benzyl viologen, bis(triphenylphosphine)iminium, metal complexes, bipyridyl metal complexes, phenanthroline-based metal complexes, [Ru(bipyridine)$_3$]$^{2+}$ and [Fe(phenanthroline)$_3$]$^{3+}$.

In one preferred embodiment, the hydrophobic cations are ammonium-based cations. In particular, the hydrophobic cations are quaternary ammonium cations. In another embodiment, the quaternary ammonium cations are represented by Formula 4:

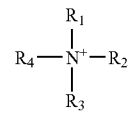

4 wherein $R_1$, $R_2$, $R_3$, and $R_4$ are independently hydrogen, hydrocarbyl, substituted hydrocarbyl, or heterocyclo wherein at least one of $R_1$, $R_2$, $R_3$, and $R_4$ is other than hydrogen. In a further embodiment, preferably, $R_1$, $R_2$, $R_3$, and $R_4$ are independently hydrogen, methyl, ethyl, propyl, butyl, pentyl, hexyl, heptyl, octyl, nonyl, decyl, undecyl, dodecyl, tridecyl or tetradecyl wherein at least one of $R_1$, $R_2$, $R_3$, and $R_4$ is other than hydrogen. In still another embodiment, $R_1$, $R_2$, $R_3$, and $R_4$ are the same and are methyl, ethyl, propyl, butyl, pentyl or hexyl. In yet another embodiment, preferably, $R_1$, $R_2$, $R_3$, and $R_4$ are butyl. Preferably, the quaternary ammonium cation is tetrapropylammonium (T3A), tetrapentylammonium (T5A), tetrahexylammonium (T6A), tetraheptylammonium (T7A), trimethylicosylammonium (TMICA), trimethyloctyldecylammonium (TMODA), trimethylhexyldecylammonium (TMHDA), trimethyltetradecylammonium (TMTDA), trimethyloctylammonium (TMOA), trimethyldodecylammonium (TMDDA), trimethyldecylammonium (TMDA), trimethylhexylammonium (TMHA), tetrabutylammonium (TBA), triethylhexylammonium (TEHA), and combinations thereof.

Exemplary micellar or inverted micellar enzyme immobilization materials are, hydrophobically modified polysaccharides, these polysaccharides are selected from chitosan, cellulose, chitin, starch, amylose, alginate, and combinations thereof. In various embodiments, the micellar or inverted micellar enzyme immobilization materials are polycationic polymers, particularly, hydrophobically modified chitosan. Chitosan is a poly[β-(1-4)-2-amino-2-deoxy-D-glucopyranose]. Chitosan is typically prepared by deacetylation of chitin (a poly[β-(1-4)-2-acetamido-2-deoxy-D-glucopyranose]). The typical commercial chitosan has approximately 85% deacetylation. These deacetylated or free amine groups can be further functionalized with hydrocarbyl, particularly, alkyl groups. Thus, in various embodiments, the micellar hydrophobically modified chitosan corresponds to the structure of Formula 1

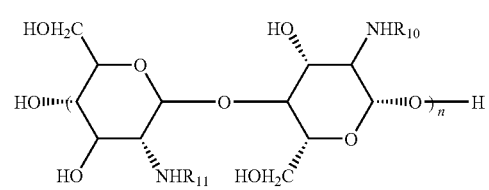

1 wherein n is an integer; $R_{10}$ is independently hydrogen, hydrocarbyl, or substituted hydrocarbyl; and $R_{11}$ is independently hydrogen, hydrocarbyl, or substituted hydrocarbyl. In certain embodiments of the invention, n is an integer that gives the polymer a molecular weight of from about 21,000 to about 500,000; preferably, from about 90,000 to about 500,000; more preferably, from about 150,000 to about 350,000;

more preferably, from about 225,000 to about 275,000. In many embodiments, $R_{10}$ is independently hydrogen or alkyl and $R_{11}$ is independently hydrogen or alkyl. Further, $R_{10}$ is independently hydrogen or hexyl and $R_{11}$ is independently hydrogen or hexyl. Alternatively, $R_{10}$ is independently hydrogen or octyl and $R_{11}$ is independently hydrogen or octyl.

Further, in various embodiments, the micellar hydrophobically modified chitosan is modified chitosan corresponding to Formula 1 B

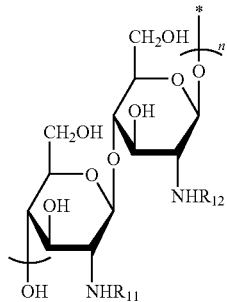

1B wherein $R_{11}$, $R_{12}$, and n are defined as in connection with Formula 1. In some embodiments, $R_{11}$ and $R_{12}$ are independently hydrogen or straight or branched alkyl; preferably, hydrogen, butyl, pentyl, hexyl, heptyl, octyl, nonyl, decyl, undecyl, or dodecyl. In various embodiments, $R_{11}$ and $R_{12}$ are independently hydrogen, butyl, or hexyl.

The micellar hydrophobically modified chitosans can be modified with hydrophobic groups to varying degrees. The degree of hydrophobic modification is determined by the percentage of free amine groups that are modified with hydrophobic groups as compared to the number of free amine groups in the unmodified chitosan. The degree of hydrophobic modification can be estimated from an acid-base titration and/or nuclear magnetic resonance (NMR), particularly $^1$H NMR, data. This degree of hydrophobic modification can vary widely and is at least about 1, 2, 4, 6, 8, 10, 12, 14, 16, 18, 20, 25, 30, 32, 24, 26, 28, 40, 42, 44, 46, 48%, or more. Preferably, the degree of hydrophobic modification is from about 10% to about 45%; from about 10% to about 35%; from about 20% to about 35%; or from about 30% to about 35%.

The hydrophobic group used to modify chitosan serves the dual function of (1) dictating the immobilization material's pore size and (2) modifying the chitosan's electronic environment to maintain an acceptable pore environment, both of which stabilize the enzyme. With regard to the first function of the hydrophobic group, hydrophobically modifying chitosan produces an enzyme immobilization material wherein the pore size is dependent on the size of the hydrophobic group. Accordingly, the size, shape, and extent of the modification of the chitosan with the hydrophobic group affects the size and shape of the pore. This function of the hydrophobic cation allows the pore size to be made larger or smaller or a different shape to fit a specific enzyme by varying the size and branching of the hydrophobic group.

Regarding the second function of the hydrophobic cation, the properties of the hydrophobically modified chitosan membranes are altered by modifying chitosan with hydrophobic groups. This hydrophobic modification of chitosan affects the pore environment by increasing the number of available exchange sites to proton. In addition to affecting the pH of the material, the hydrophobic modification of chitosan provides a membrane that is a mechanical barrier, which further protects the immobilized enzymes.

Table 1 shows the number of available exchange sites to proton for the hydrophobically modified chitosan membrane.

TABLE 1

| Number of available exchange sites to proton per gram of chitosan polymer | |
|---|---|
| Membrane | Exchange sites per gram ($\times 10^{-4}$ mol $SO_3$/g) |
| Chitosan | 10.5 ± 0.8 |
| Butyl Modified | 226 ± 21 |
| Hexyl Modified | 167 ± 45 |
| Octyl Modified | 529 ± 127 |
| Decyl Modified | 483 ± 110 |

Further, such polycationic polymers are capable of immobilizing enzymes and increasing the activity of enzymes immobilized therein as compared to the activity of the same enzyme in a buffer solution. In various embodiments, the polycationic polymers are hydrophobically modified polysaccharides, particularly, hydrophobically modified chitosan. For example, for the hydrophobic modifications noted, the enzyme activities for glucose oxidase were measured using the procedure in Example 6. The highest enzyme activity was observed for glucose oxidase in a hexyl modified chitosan suspended in t-amyl alcohol. These immobilization membranes showed a 2.53 fold increase in glucose oxidase enzyme activity over enzyme in buffer. Table 2 details the glucose oxidase activities for a variety of hydrophobically modified chitosans.

TABLE 2

| Glucose oxidase enzyme activity for modified chitosans | |
|---|---|
| Membrane/Solvent | Enzyme Activity (Units/gm) |
| Buffer | 103.61 ± 3.15 |
| UNMODIFIED CHITOSAN | 214.86 ± 10.23 |
| HEXYL CHITOSAN | |
| Chloroform | 248.05 ± 12.62 |
| t-amyl alcohol | 263.05 ± 7.54 |
| 50% acetic acid | 118.98 ± 6.28 |
| DECYL CHITOSAN | |
| Chloroform | 237.05 ± 12.31 |
| t-amyl alcohol | 238.05 ± 10.02 |
| 50% acetic acid | 3.26 ± 2.82 |
| OCTYL CHITOSAN | |
| Chloroform | 232.93 ± 7.22 |
| t-amyl alcohol | 245.75 ± 9.77 |
| 50% acetic acid | 127.55 ± 11.98 |
| BUTYL CHITOSAN | |
| Chloroform | 219.15 ± 9.58 |
| t-amyl alcohol | 217.10 ± 6.55 |
| 50% acetic acid | 127.65 ± 3.02 |

To prepare the hydrophobically modified chitosans of the invention having an alkyl group as a modifier, a chitosan gel was suspended in acetic acid followed by addition of an alcohol solvent. To this chitosan gel was added an aldehyde (e.g., butanal, hexanal, octanal, or decanal), followed by addition of sodium cyanoborohydride. The resulting product was separated by vacuum filtration and washed with an alcohol solvent. The modified chitosan was then dried in a vacuum oven at 40° C., resulting in a flaky white solid.

To prepare a hydrophobically modified chitosan of the invention having a redox mediator as a modifier, a redox mediator ligand was derivatized by contacting 4,4'-dimethyl-2,2'-bipyridine with lithium diisopropylamine followed by addition of a dihaloalkane to produce 4-methyl-4'-(6-haloalkyl)-2,2'-bipyridine. This ligand was then contacted with Ru(bipyridine)$_2$Cl$_2$ hydrate in the presence of an inorganic base and refluxed in a water-alcohol mixture until the Ru(bipyridine)$_2$Cl$_2$ was depleted. The product was then precipitated with ammonium hexafluorophosphate, or optionally a sodium or potassium perchlorate salt, followed by recrystallization. The derivatized redox mediator (Ru(bipyridine)$_2$(4-methyl-4'-(6-bromohexyl)-2,2'-bipyridine)$^{+2}$) was then contacted with deacetylated chitosan and heated. The redox mediator modified chitosan was then precipitated and recrystallized.

The hydrophobically modified chitosan membranes have advantageous insolubility in ethanol. For example, the chitosan enzyme immobilization materials described above generally are functional to immobilize and stabilize the enzymes in solutions having up to greater than about 99 wt. % or 99 volume % ethanol. In various embodiments, the chitosan immobilization material is functional in solutions having 15, 20, 25, 30, 35, 40, 45, 50, 55, 60, 65, 70, 75, 80, 85, 90, 95 or more wt. % or volume % ethanol.

In other embodiments, the micellar or inverted micellar enzyme immobilization materials are polyanionic polymers, such as hydrophobically modified polysaccharides, particularly, hydrophobically modified alginate. Alginates are linear unbranched polymers containing β-(1-4)-linked D-mannuronic acid and α-(1-4)-linked L-guluronic acid residues. In the unprotonated form, β-(1-4)-linked D-mannuronic acid corresponds to the structure of Formula 3A

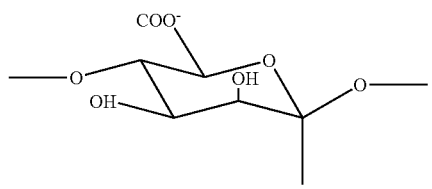

3A and in the unprotonated form, α-(1-4)-linked L-guluronic acid corresponds to the structure of Formula 3B

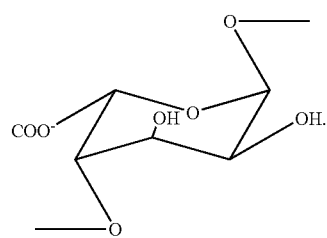

3B

Alginate is a heterogeneous polymer consisting of polymer blocks of mannuronic acid residues and polymer blocks of guluronic acid residues.

Alginate polymers can be modified in various ways. One type is alginate modified with a hydrophobic cation that is larger than the ammonium (NH$_4^+$) ion. The hydrophobic cation serves the dual function of (1) dictating the polymer's pore size and (2) acting as a chemical buffer to help maintain the pore's pH level, both of which stabilize the enzyme. With regard to the first function of the hydrophobic cation, modifying alginate with a hydrophobic cation produces an enzyme immobilization material wherein the pore size is dependent on the size of the hydrophobic cation. Accordingly, the size, shape, and extent of the modification of the alginate with the hydrophobic cation affects the size and shape of the pore. This function of the hydrophobic cation allows the pore size to be made larger or smaller or a different shape to fit a specific enzyme by varying the size and branching of the hydrophobic cation.

Regarding the second function of the hydrophobic cation, the properties of the alginate polymer are altered by exchanging the hydrophobic cation for protons as the counterion to the —CO$_2^-$ groups on the alginate. This change in counterion provides a buffering effect on the pH because the hydrophobic cation has a much greater affinity for the —CO$_2^-$ sites than protons do. This buffering effect of the alginate membrane causes the pH of the pore to remain substantially unchanged with changing solution pH; stated another way, the pH of the pore resists changes in the solution's pH. In addition, the alginate membrane provides a mechanical barrier, which further protects the immobilized enzymes.

In order to prepare a modified alginate membrane, the first step is to cast a suspension of alginate polymer with a solution of the hydrophobic cation to form a membrane. The excess hydrophobic cations and their salts are then extracted from the membrane, and the membrane is re-cast. Upon re-casting, the membrane contains the hydrophobic cations in association with —CO$_2^-$ sites of the alginate membrane. Removal of the salts of the hydrophobic cation from the membrane results in a more stable and reproducible membrane since the excess salts can become trapped in the pore or cause voids in the membrane In one embodiment, a modified alginate membrane is prepared by casting a suspension of alginate polymer with a solution of a salt of a hydrophobic cation such as quaternary ammonium bromide. Excess quaternary ammonium bromide or hydrogen bromide are removed from the membrane before it is re-cast to form the salt-extracted membrane. Salt extraction of membranes retains the presence of the quaternary ammonium cations at the carboxylic acid exchange sites, but eliminates complications from excess salt that may be trapped in the pore or may cause voids in the equilibrated membrane. Exemplary hydrophobic cations are ammonium-based cations, quaternary ammonium cations, alkyltrimethylammonium cations, alkyltriethylammonium cations, organic cations, phosphonium cations, triphenylphosphonium, pyridinium cations, imidazolium cations, hexadecylpyridinium, ethidium viologens, methyl viologen, benzyl viologen, bis(triphenylphosphine)iminium, metal complexes, bipyridyl metal complexes, phenanthroline-based metal complexes, [Ru(bipyridine)$_3$]$^{2+}$ and [Fe(phenanthroline)$_3$]$^{3+}$.

In one preferred embodiment, the hydrophobic cations are ammonium-based cations. In particular, the hydrophobic cations are quaternary ammonium cations. In another embodiment, the quaternary ammonium cations are represented by Formula 4:

4

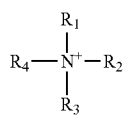

wherein $R_1$, $R_2$, $R_3$, and $R_4$ are independently hydrogen, hydrocarbyl, substituted hydrocarbyl, or heterocyclo wherein at least one of $R_1$, $R_2$, $R_3$, and $R_4$ is other than hydrogen. In a further embodiment, preferably, $R_1$, $R_2$, $R_3$, and $R_4$ are independently hydrogen, methyl, ethyl, propyl, butyl, pentyl, hexyl, heptyl, octyl, nonyl, decyl, undecyl, dodecyl, tridecyl or tetradecyl wherein at least one of $R_1$, $R_2$, $R_3$, and $R_4$ is other than hydrogen. In still another embodiment, $R_1$, $R_2$, $R_3$, and $R_4$ are the same and are methyl, ethyl, propyl, butyl, pentyl or hexyl. In yet another embodiment, preferably, $R_1$, $R_2$, $R_3$, and $R_4$ are butyl. Preferably, the quaternary ammonium cation is tetrapropylammonium (T3A), tetrapentylammonium (T5A), tetrahexylammonium (T6A), tetraheptylammonium (T7A), trimethylicosylammonium (TMICA), trimethyloctyldecylammonium (TMODA), trimethylhexyldecylammonium (TMHDA), trimethyltetradecylammonium (TMTDA), trimethyloctylammonium (TMOA), trimethyldodecylammonium (TMDDA), trimethyldecylammonium (TMDA), trimethylhexylammonium (TMHA), tetrabutylammonium (TBA), triethylhexylammonium (TEHA), and combinations thereof.

Figure 11:
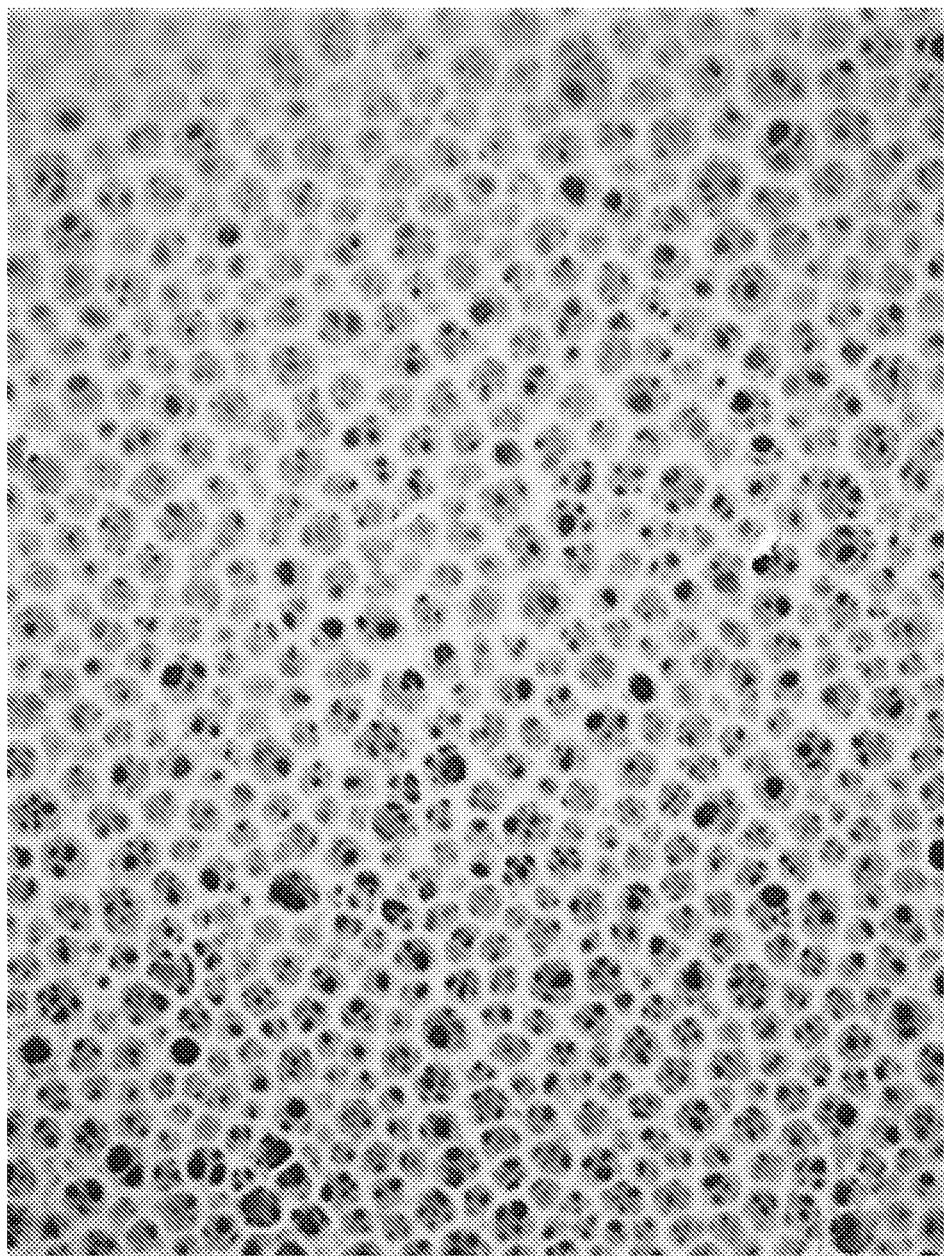
FIG. 11 is a fluorescence micrograph of a low molecular weight alginate modified with tetrapentylammonium ions.
Figure 12:
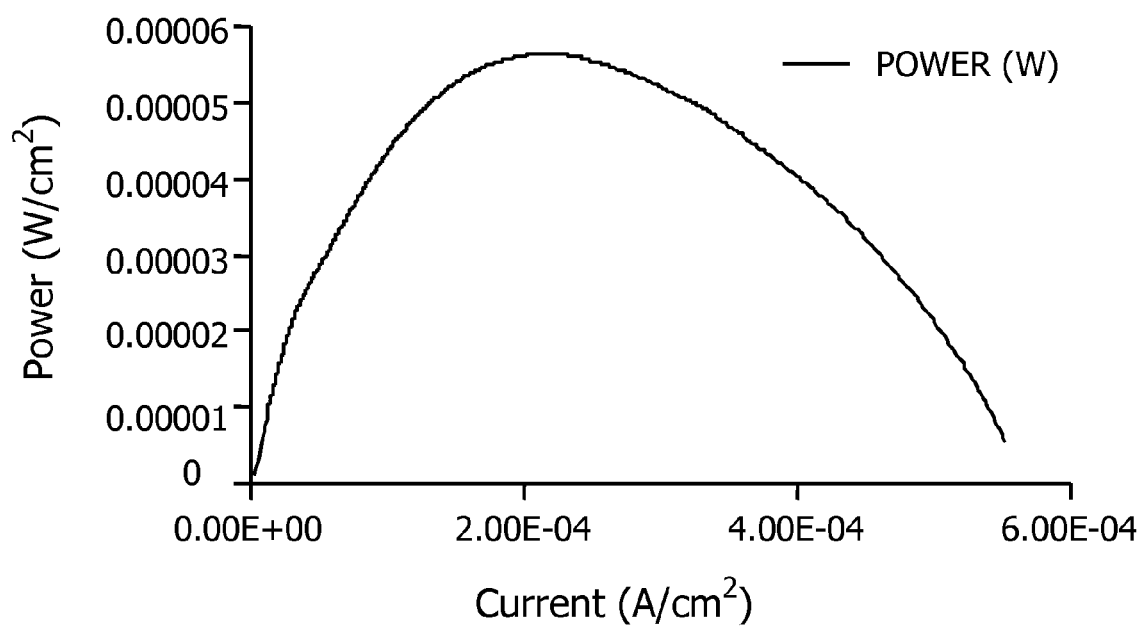
FIG. 12 shows power curves for direct electron transfer biocathodes comprising trimethyloctylammonium (TMOA)-modified Nafion® and superoxide dismutase.

The pore characteristics were studied and the results for one hydrophobically modified alginate membrane are shown in FIG. 11. The pore structure of this membrane is ideal for enzyme immobilization, because the pores are hydrophobic, micellar in structure, buffered to external pH change, and have high pore interconnectivity.

In another experiment, ultralow molecular weight alginate and dodecylamine were placed in 25% ethanol and refluxed to produce a dodecyl-modified alginate by amidation of the carboxylic acid groups. Various alkyl amines can be substituted for the dodecylamine to produce alkyl-modified alginate having a $C_4$-$C_{16}$ alkyl group attached to varying numbers of the reactive carboxylic acid groups of the alginate structure. In various embodiments, at least about 1, 2, 4, 6, 8, 10, 12, 14, 16, 18, 20, 22, 24, 26, 28, 30, 32, 34, 36, 38, 40, 42, 44, 46, 48%, or more of the carboxylic acid groups react with the alkylamine.

The hydrophobically modified alginate membranes have advantageous insolubility in ethanol. For example, the alginate enzyme immobilization materials described above generally are functional to immobilize and stabilize the enzymes in solutions having at least about 25 wt. % or 25 volume % ethanol. In various embodiments, the alginate immobilization material is functional in solutions having 25, 30, 35, 40, 45, 50, 55, 60, 65, 70, 75, 80, 85, 90 or more wt. % or volume % ethanol.

4. Biocathode Embodiments

Various biocathodes can be incorporated into the biofuel cells of the present invention. For example, such biocathodes are described in U.S. patent application Ser. No. 10/931,147 (published as U.S. Patent Application Publication No. 2005/0095466), herein incorporated by reference in its entirety.

B. Bioanode

In one embodiment, the bioanode comprises an electron conductor and an enzyme which is immobilized in an enzyme immobilization material. The above-identified components of the bioanode are adjacent to one another; meaning they are physically or chemically connected by appropriate means. As the components are generally the same as the biocathode components, the following discussion concerns the differences in composition of the respective elements and differences in function, where appropriate.

1. Electron Conductor

As with the biocathode, the bioanode's electron conductor can be organic or inorganic in nature as long as it is able to conduct electrons through the material. In one embodiment, the bioanode electron conductor is carbon paper.

2. Enzyme

An enzyme catalyzes the oxidation of the fuel fluid at the bioanode. Specifically, exemplary enzymes for use in a bioanode are enzymes that react to oxidize the fuel fluid and comprise more than one redox center. For example, a suitable anode enzyme comprises a PQQ-dependent dehydrogenase, a lipoxygenase, or combinations thereof. The PQQ-dependent alcohol dehydrogenase enzyme is extracted from gluconobacter.

3. Enzyme Immobilization Material

As described above, an enzyme immobilization material is utilized in the biofuel cell at the bioanode and/or the biocathode. Further detail regarding the composition of the enzyme immobilization material and the immobilization mechanism can be found above at I.A.3. In one embodiment, the bioanode's enzyme immobilization material is permeable to the fuel fluid and immobilizes and stabilizes the enzyme. The immobilization material is permeable to the fuel fluid so the oxidation of the fuel fluid at the bioanode can be catalyzed by the immobilized enzyme. In some embodiments, the enzyme immobilization material is a hydrophobically modified polysaccharide, particularly, a hydrophobically modified chitosan.

4. Bioanode Embodiments

A preferred bioanode is described in U.S. patent application Ser. No. 10/617,452 (published as U.S. Patent Application Publication No. 2004/0101741), which is incorporated herein by reference in its entirety. Other potentially useful bioanodes are described in U.S. Pat. Nos. 6,531,239 and 6,294,281, which are also incorporated herein by reference.

C. Fuel Fluid and Oxidant

A fuel fluid that can be oxidized to produce electrons at the bioanode and an oxidant that can be reduced to produce water at the biocathode are components of the biofuel cell of this invention.

The fuel fluid for the bioanode is consumed in the oxidation reaction of a redox center of the immobilized enzyme. The fuel fluid's molecular size is small enough so the diffusion coefficient through the enzyme immobilization material is large. Exemplary fuel fluids are hydrogen, ammonia, alcohols (such as methanol, ethanol, propanol, isobutanol, butanol and isopropanol), allyl alcohols, aryl alcohols, glycerol, propanediol, mannitol, glucuronate, aldehyde, carbohydrates (such as glucose, glucose-1, D-glucose, L-glucose, glucose-6-phosphate, lactate, lactate-6-phosphate, D-lactate, L-lactate, fructose, galactose-1, galactose, aldose, sorbose and mannose), glycerate, coenzyme A, acetyl Co-A, malate, isocitrate, formaldehyde, acetaldehyde, acetate, citrate, L-gluconate, beta-hydroxysteroid, alpha-hydroxysteroid, lactaldehyde, testosterone, gluconate, fatty acids, lipids, phosphoglycerate, retinal, estradiol, cyclopentanol, hexadecanol, long-chain alcohols, coniferyl-alcohol, cinnamyl-alcohol, formate, long-chain aldehydes, pyruvate, butanal, acyl-CoA, steroids, amino acids, flavin, NADH, $NADH_2$, NADPH, $NADPH_2$, hydrocarbons, and amines. In various preferred embodiments, the fuel fluid is an alcohol, more preferably methanol and/or ethanol; and most preferably ethanol.

The oxidant for the biocathode is consumed in the reduction reaction of a redox center of the immobilized enzyme using electrons supplied by the bioanode. The oxidant's molecular size is small enough so the diffusion coefficient through the enzyme immobilization material is large. A variety of means of supplying a source of the oxidant known in the art can be utilized.

In preferred embodiments, the oxidant is gaseous oxygen, which is transported to the biocathode via diffusion. In other preferred embodiments, the oxidant is a peroxide compound.

The biofuel cells of the embodiments can comprise (i) a bioanode as described above; (ii) a biocathode as described above; (iii) a bioanode and a biocathode as described above; (iv) a bioanode as described above and a biocathode as described in U.S. patent application Ser. No. 10/931,147 (published as U.S. Patent Application Publication No. 2005/0095466); and (v) a bioanode as described in U.S. patent application Ser. No. 10/617,452 (published as U.S. Patent Application Publication No. 2004/0101741) and a biocathode as described above.

The biofuel cell of the instant invention may comprise a polymer electrolyte membrane ("PEM" or salt bridge, e.g., Nafion® 117) to separate the anode compartment from the cathode compartment. However, for embodiments having a bioanode and a biocathode, a PEM is not necessary and a membraneless biofuel cell is produced. The preferential selectivity of the enzymes used in the bioanode and biocathode for catalysis of either the oxidant or the fuel fluid reaction makes the physical separation of the anode compartment from the cathode compartment unnecessary.

II. Microfluidic Biofuel Cell

Among the various aspects of the invention is a microfluidic biofuel cell utilizing a fuel fluid to produce electricity via enzyme mediated redox reactions taking place at micromolded microelectrodes with immobilized enzymes therein. As in a standard biofuel cell, the bioanode is the site for an oxidation reaction of a fuel fluid with a concurrent release of electrons. The electrons are directed from the bioanode through an electrical connector to some power consuming device. The electrons move through the device to another electrical connector, which transports the electrons to the biofuel cell's biocathode where the electrons are used to reduce an oxidant to produce water. In this manner, the biofuel cell of the present invention acts as an energy source (electricity) for an electrical load external thereto. To facilitate the fuel fluid's redox reactions, the microelectrodes comprise an electron conductor, an enzyme, and an enzyme immobilization material.

Unlike a standard biofuel cell, however, the biofuel cell of the invention utilizes at least one micromolded electrode. In one embodiment, the micromolded electrode has a flow through structure that allows fuel to flow within the microelectrode. When compared to conventional biofuel cell electrodes, this structure yields a higher current density because of the higher amount of microelectrode surface area in contact with the fuel. In another embodiment, the micromolded electrode has an irregular topography. Again, the current density of the microelectrode is greater than conventional biofuel cell electrodes because of a higher amount of surface area in contact with the fuel. These features combine with other features disclosed herein to create a biofuel cell with increased current density over conventional biofuel cells from a dimensionally smaller source. Finally, the method of the current invention can advantageously be used to economically produce disposable fuel cells.

A. Microfluidic Channel

Beyond the bioanode and/or biocathode, the microfluidic biofuel cell is characterized by at least one microfluidic channel that, in service, houses the bioanode and/or the biocathode, the fuel fluid, and the oxidant. The microfluidic channel's configuration can vary depending on the application. In one embodiment, the microfluidic channel can simply be a rectangular chamber with the bioanode and/or the biocathode of the biofuel cell contained therein. See FIG. 2. In other embodiments, the configuration of the microfluidic channel can be more elaborate for any desired purpose, such as to ensure that the bioanode solution and the biocathode solution do not come into physical contact with one another. See FIG. 3.

Figure 2:
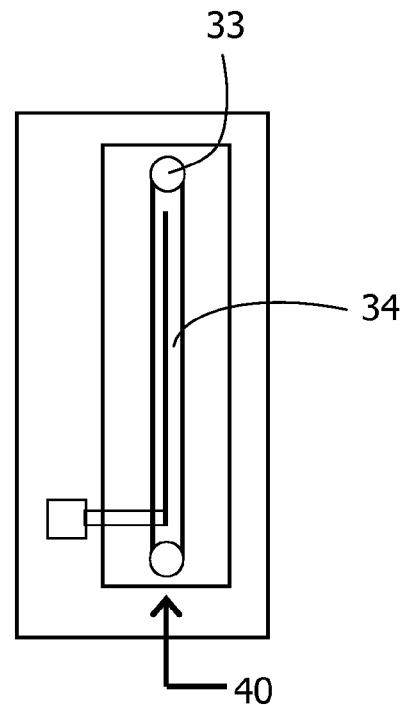
FIG. 2 shows a single, functional bioanode or biocathode.
Figure 3:
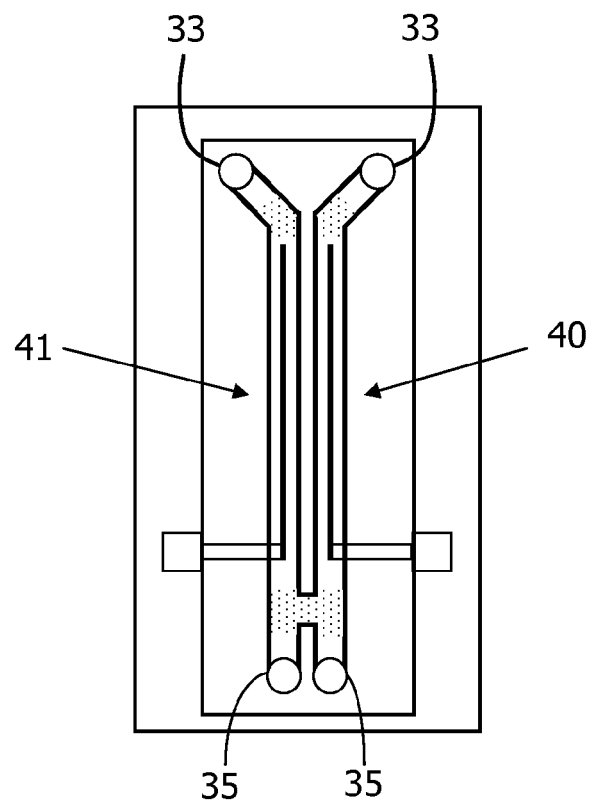
FIG. 3 shows a microfluidic biofuel cell.

With reference to FIGS. 2 and 3, the fuel fluid and/or oxidant flow through the microfluidic channel (34), over or through the microelectrode(s), from one end of the microfluidic channel (entry) (33) to the opposite end (exit) (35). In FIG. 3, the bioanode is represented by (41) and the biocathode is represented by (40). The microfluidic channel should facilitate convective flow of the fuel fluid and/or oxidant over the microelectrode(s) while preventing leakage of the same outside the microfluidic channel (34).

B. Electrical Connectors

The electrical connectors provide electrical contact from the microelectrodes to the electrical load external to the microfluidic biofuel cell. In the most general sense, the electrical connector can be any material and structure that facilitates the transfer of electrons from the bioanode to the electrical load and back to the biocathode. In one preferred embodiment, the electrical connector of the microfluidic biofuel cell provide attachment leads to which another device can make physical and electrical contact. This other device, e.g. copper wire, then transports electrons are transported to and from the external electrical load.

In one preferred embodiment, the electrical connector is a thin layer connector that is formed on the microfluidic biofuel cell's substrate prior to other processing. In this embodiment, the subsequently formed microelectrodes are arranged such that they intersect their respective electrical connectors. In an alternative embodiment, the electrical connector is a cylindrical body of electrically conductive material that is attached to the microelectrodes subsequent to their processing.

III. Microfluidic Biofuel Cell Fabrication

In fabricating a microfluidic biofuel cell in accordance with this invention, a substrate is used on which the other biofuel cell components are constructed. In a preferred embodiment, the first step is to form the electrical connectors, followed by the fabrication of the microelectrodes, and the optional step of defining a biofuel chamber. In an alternative embodiment, the electrical connectors are formed subsequent to the other features.

A. Fabrication of Electrical Connectors

The microfluidic biofuel cell of the invention is formed by providing a substrate onto which the remaining components are formed. The substrate can be made of any material that is not conductive, will not passivate the conductive material of the microelectrode, to which the conductive material will adhere throughout processing, and to which molds can be reversibly sealed. In one embodiment, the substrate is glass. In a preferred embodiment, the substrate is poly(dimethylsiloxane) (PDMS). In another preferred embodiment, the substrate is polycarbonate. In one embodiment, the substrate is flat. In alternative embodiments, the substrate can take on a geometric shape that advantageously suits the particular application.

In a preferred embodiment, the first biofuel cell feature formed on the substrate is an electrical connector, which will be in electrical contact with the microelectrodes in the completed biofuel cell to provide the means for connecting the external electrical load to the microelectrodes. The connector can be made of any electrically conductive material. Exemplary materials include platinum, palladium, gold, alloys of those precious metals, carbon, nickel, copper and stainless steel. In a preferred embodiment, the connector is made of platinum.

The connector can be formed on the substrate using conventional photolithographic techniques known in the silicon wafer industry. For example, to form a thin layer platinum electrical connector, a titanium adhesion layer is first sputtered onto the substrate. This is followed by sputtering a layer of platinum over the titanium layer. Both sputtering processes can be carried out, for example, in an argon-ion sputtering system. The connectors will then be defined by photolithography, with photoresist applied to the platinum layer to protect the desired connector locations. Chemical etching of the two layers with commercially available etchants followed by stripping of the photoresist will yield the finished platinum electrical connectors. In an alternative embodiment, the electrical connectors are the last feature formed. This embodiment is detailed below.

B. Fabrication of Microelectrodes

Following the creation of electrical connectors on the biofuel cell's substrate, the next step is the fabrication of the bioanode and the biocathode. These can be formed in succession or simultaneously.

1. Bioanode Fabrication

In one embodiment, the bioanode and the biocathode are formed on the substrate in succession, where the order of formation is not critical. For the purposes of presentation only, the bioanode fabrication will be detailed first. The first step of fabricating a microscale bioanode is creating a pattern of a microchannel in the surface of a casting mold. In general, the casting mold can be made of any material that is not conductive, will not passivate the conductive material and is able to be reversibly sealed to the substrate, with exemplary materials including silicon, glass, and polymers. The casting mold is preferably made of a polymer, even more preferably made of PDMS. Most preferably, the casting mold is made of polycarbonate.

In a preferred embodiment where the casting mold is a polymer, the pattern is created by using known soft lithography techniques to produce the microchannel in the casting mold to define the shape and size of the bioanode. Soft lithography techniques generally entail the process of molding a prepolymer against a lithographically-defined master that has a raised image of the desired design. The soft lithography technique employed should be able to yield microchannels in the casting mold between about 1 µm to about 1 mm, between about 1 µm to about 200 µm, preferably between about 10 µm to about 200 µm, more preferably between about 10 µm to about 100 µm, and most preferably as small as about 10 µm or less. Exemplary soft lithography techniques include near-field phase shift lithography, replica molding, microtransfer molding (µTM), solvent-assisted microcontact molding (SAMIM), and microcontact printing (µCP). Preferably, the microchannels are formed using replica molding.

Figure 4A:
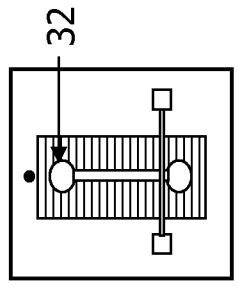
FIG. 4(a)-(d) shows the procedure for forming a single microelectrode.

After the microchannel is formed in the casting mold, the patterned side of the casting mold is adhered to the substrate to complete the mold of the microelectrode. See FIG. 4(a). In the embodiment where the electrical connector (31) has previously been formed on the substrate, the microchannel should align over the electrical connector such that the finished microelectrode will be in electrical contact with the connector. Further, a tubing connector (30) is adhered to the substrate to maintain the position that will later become the entry reservoir.

Figure 4B:
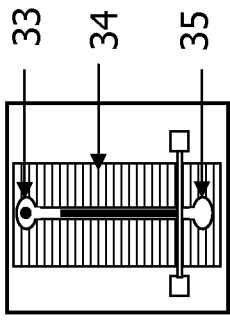

Next, with reference to FIG. 4(b), an electron conductor solution is flowed into the casting mold's microchannel through an entry reservoir (32) that has been created in the casting mold at one end of the microchannel. This entry reservoir (32) is analogous to a pouring basin in the traditional art of metal casting. Excess solution will exit the microchannel at a vent located at the end of the microchannel opposite the entry reservoir.

The electron conductor solution can be any solution that comprises an electron conductor source and a liquid carrier that can be removed via curing to yield a solid microelectrode. The numerous potential electron conductor materials are listed above in I.A.1. In one preferred embodiment, the electron conductor source is a carbon source. In a more preferred embodiment, the electron conductor source is a carbon-based ink. In one such embodiment, the liquid carrier is a carbon-based ink thinner, e.g., Ercon N160 Solvent Thinner. Depending on the nature of the liquid carrier in the solution, two types of microelectrode structures can be formed according to the invention—solid microelectrodes or flow through microelectrodes. With lower viscosity liquid carriers, solid microelectrodes are produced. These microelectrodes are substantially continuous and solid, and fuel fluid flows over such microelectrodes during use. With higher viscosity liquid carriers, flow through microelectrodes are produced with a structure enabling fuel fluid to flow therethrough during use, effectively increasing the surface area of the microelectrode in contact with the fuel fluid.

Regardless of the particular structure, a microelectrode formed in accordance with this invention has several advantages over microelectrodes formed using traditional processes, which necessarily have flat topography. As such, any fluid flowing over conventional microelectrodes has a generally regular flow pattern and is in contact with a generally defined amount of microelectrode surface area. This flat geometric surface area is calculated by adding the rectangular surface area of the top and sides of the flat microelectrode. As current production of a microelectrode is determined in large part by the surface area in contact with the fuel fluid, a flat microelectrode's current production capabilities can only be increased by increasing its size. In contrast, microelectrodes formed in accordance with this invention have highly irregular, three dimensional topography, which yields at least two distinct advantages. First, the effective surface area of the invention's microelectrode is substantially increased compared to a flat screen printed microelectrode. The effective surface area of the microelectrodes herein described is the sum of surface area of the individual peaks and valleys characterizing the microelectrode's topography. One accurate method of calculating this effective surface area is to compare the current output of a microelectrode formed according to the invention with a flat microelectrode of the same length, width, and height dimensions. For example, such analysis of microelectrodes has shown current output of $9.85 \times 10^4$ A/cm$^2$ for a microelectrode of this invention, compared to $2.06 \times 10^{-4}$ A/cm$^2$ for a conventional glassy carbon electrode. Further, the microelectrode's irregular topography can create turbulent flow of the fluid. Such a flow pattern is advantageous because it induces mixing of the fluid over the microelectrode, which in turn increases the transport rate of the fluid to the microelectrode. Increasing the transport rate of the fluid facilitates the reactions taking place within the microelectrode, thereby increasing the microelectrode's current load capability.

In one alternative embodiment, a primer is flowed into the casting mold's microchannels and quickly dried prior to introducing the electron conductor solution. The primer can be any material that will help prevent the electron conductor from becoming semi-permanently attached to the casting mold. For example, in the carbon-based ink embodiment, carbon-based ink thinner can be used as a primer, if one is desired.

Figure 4C:
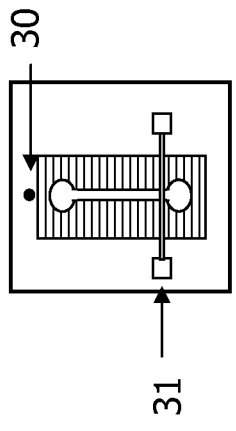

After the solution fills the casting mold's microchannels, heat is applied to cure the electron conductor solution. In general, heating should be conducted at a temperature sufficient to remove the liquid carrier from the solution, but low enough so that the resulting microelectrode is not damaged. In one preferred embodiment, heating occurs at about 75° C. Also, heat should be applied for a time sufficient to remove substantially all of the liquid carrier from the solution. In one preferred embodiment, heat is applied for at least about one hour. In another preferred embodiment, heating occurs at about 75° C. for about one hour. With reference to FIG. 4(c), the curing process yields a solidified microelectrode (36) that is approximately 20% smaller than the original size of the casting mold's microchannel(s) due to evaporation of the carrier.

Figure 4D:
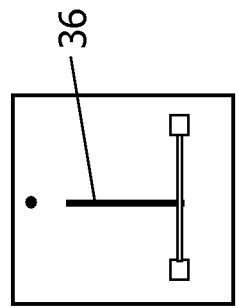

In the method according to the invention, the microelectrode is treated to impart an enzyme, and an enzyme immobilization material thereto to form a bioanode. In certain embodiments, the enzyme immobilization material containing the enzyme is applied to the cured microelectrode. To form the bioanode, the casting mold is removed from the substrate after curing the microelectrode. See FIG. 4(c). With reference to FIG. 4(d), in place of the casting mold, a gas-permeable mold with a microchannel (34) approximately twice the width of the casting mold's microchannel is reversibly sealed over the microelectrode. The gas-permeable mold can be made of any material that is not conductive, will not passivate the electron conductor and facilitates evaporation of a solvent. Preferably, a silicon polymer, such as PDMS, is used as the gas-permeable mold material. More preferably, a thermoplastic resin, such as polycarbonate, is the gas-permeable mold material. After the gas-permeable mold is in place, an enzyme immobilization material containing a bioanode enzyme is applied to the cured microelectrode. This is accomplished by syringe pumping the casting solution into the entry reservoir (33) and through the gas-permeable mold to an exit vent (35). See FIG. 4(d) for a finished bioanode.

In all embodiments, the specific composition of the enzyme immobilization material, the enzyme, is detailed above in I.B.2.-I.B.3. Preferred enzyme immobilization materials for the bioanode is a tetraalkyl ammonium-modified perfluoro sulfonic acid-PTFE copolymer or a hydrophobically modified polysaccharide, particularly, a hydrophobically modified chitosan. The preferred enzyme at the anode is a PQQ-dependent dehydrogenase. Also, the casting mold can include more than one microchannel in all embodiments.

2. Biocathode Fabrication

To form a biocathode in accordance with the invention, the same general processing steps taken to fabricate the bioanode can be used to produce a biocathode. The embodiments for treating the biocathode with the enzyme immobilization material, and the enzyme are the same as those for the bioanode. The specific composition of the enzyme immobilization material, and the enzyme is detailed above in I.A.2.-I.A.3. The preferred enzyme immobilization material for the biocathode is a tetraalkyl ammonium-modified perfluoro sulfonic acid-PTFE copolymer or a hydrophobically modified polysaccharide, particularly, a hydrophobically modified chitosan. Additionally for the biocathode, the preferred enzyme is bilirubin oxidase.

3. Forming the Operational Biofuel Cell

After the bioanode and biocathode have been formed in accordance with this invention, the casting or gas-permeable molds are optionally removed. In this optional embodiment the bioanode and biocathode remain on the substrate. After the casting or gas-permeable molds are removed, a microfluidic channel form is aligned over the bioanode and biocathode. This form is micropatterned so as to create at least one microfluidic channel through which the biofuel cell's fuel fluid can flow. The form can be made of any material that is not conductive, will not passivate the conductive material and will adhere to the substrate. Preferably, the form is PDMS. More preferably, this overlay is polycarbonate. The micropatterns of the microfluidic channel(s) in the form can be created by using any known soft lithography technique. In one embodiment, the microfluidic channel is about two to four times larger than the microelectrodes. In another embodiment, the microfluidic channel is approximately the same size as the microelectrodes. The microfluidic channels of the form essentially define the electrochemical cell in which the fuel fluid will interface with the microelectrodes. When only one microfluidic channel is used to house the bioanode, biocathode, fuel fluid, and oxidant, the mixture of fuel fluid and oxidant in the same microfluidic chamber does not compromise the function of the microelectrodes of the invention because their redox reactions are selective. Stated another way, the bioanode will only react with fuel fluid and the biocathode will only react with the oxidant, and no cross reaction takes place.

In an alternative embodiment, the casting or gas-permeable mold(s) remain in contact with the substrate and serves to define the microfluidic channels of the biofuel cell, acting as the microfluidic channel form described above. In this embodiment, the fuel fluid travels through the space between the microchannels of the mold(s) and the bioanode or biocathode. In this embodiment, subsequent processing must be performed to create a junction between the individual bioanode and biocathode microfluidic channels. To form the junction, a passage connecting the individual microfluidic chambers is formed in the mold(s) by any appropriate means, such as applying a perpendicular force to the top of the mold(s) or removing sufficient material from the mold(s). Thereafter, the passage is covered by a material that will seal the junction to inhibit leakage of the fuel fluid or oxidant during operation. The material must be capable of being joined to the mold material to create the appropriate seal. In one embodiment, the covering material is simply a flat piece of the mold material, such as PDMS or polycarbonate.

4. Optional Formation Embodiments

The microelectrode fabrication technique described above in III.B.1. refers to the embodiment wherein the bioanode and the biocathode were formed successively, which was followed by a method of connecting the bioanode and biocathode via microchannels to form the biofuel cell. In an alternative embodiment, the bioanode and the biocathode can be formed simultaneously. In this embodiment, a single casting mold is patterned to form both the bioanode and biocathode. Alternatively, a combination of casting molds can be used to form the individual bioanode and biocathode. In either case, after the bioanode and biocathode are simultaneously formed, the operational biofuel cell is formed by either applying a microfluidic channel form or modifying the casting mold(s) as detailed above in III.B.3.

The embodiment described above in II.A. describes the formation of the electrical connectors on the substrate prior to other processing steps. In an alternative embodiment, the electrical connectors are added to the microfluidic biofuel cell as a final processing step. Here, holes are created in the microfluidic channel form or the modified casting mold(s) to expose a portion of each bioanode and biocathode. Next, electrical connectors are physically joined to the exposed portion of each bioanode and biocathode. In this embodiment, the electrical connectors can be any material in any structure that will enable the external electrical load to make electrical contact with the bioanode and biocathode. In one preferred embodiment, the electrical connectors are cylindrical copper bodies. Further, any joining technique capable of maintaining the electrical contact between the electrical connectors and the bioanode and biocathode can be employed. In one preferred embodiment, silver epoxy paste can be used to join the electrical connectors and the bioanode and biocathode electrically. This embodiment has the advantage of increasing the conductivity between these components.

The above embodiments have described a biofuel cell wherein both the bioanode and the biocathode are housed within the microchannel(s) of the biofuel cell. While this is the preferred embodiment, alternative embodiments of the invention include an anode or a cathode located external to the microchannel(s) of the biofuel cell. Here, a fuel cell is formed by combining a microfluidic bioanode or biocathode with the appropriate external anode or cathode.

C. Use of the Microfluidic Biofuel Cell

After fabrication of the operational microfluidic biofuel cell of this invention is complete, it can be utilized in myriad applications where a fluid fuel source and oxidant are available for the bioanode and biocathode respectively. In use, the fuel fluid and the oxidant travel through the microfluidic channel(s) to contact the bioanode and biocathode. There, the redox reactions described above at 1. take place to create a current source. The microfluidic biofuel cell of the instant invention may be used in any application that requires an electrical supply, such as electronic devices, commercial toys, internal medical devices, and electrically powered vehicles. Further, the microfluidic biofuel cell of the instant invention may be implanted into a living organism, wherein the fuel fluid is derived from the organism and current is used to power a device implanted in the living organism.

Figure 5:
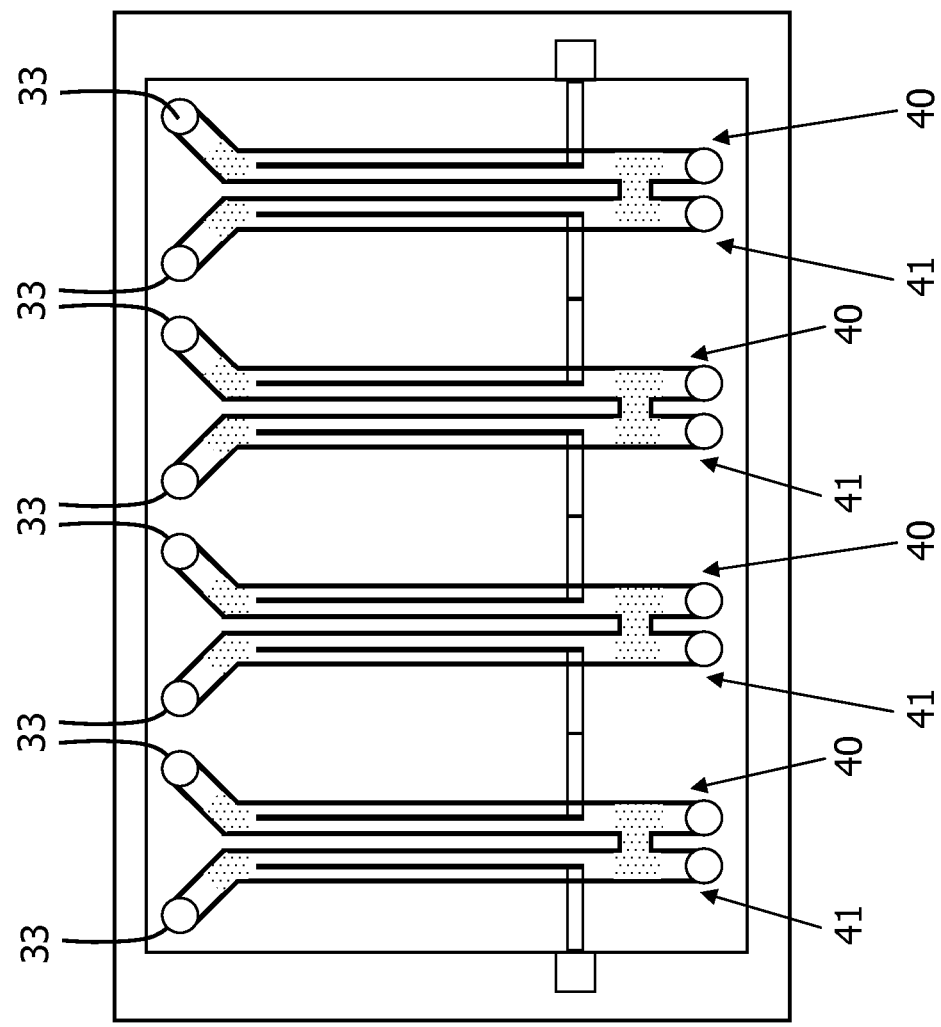
FIG. 5 shows a microfluidic biofuel cell stack.

In addition, multiple microfluidic biofuel cells of the invention can be joined in a series electrical circuit to form a biofuel cell stack. See FIG. 5. A series stack is formed by electrically joining the bioanode (41) of one biofuel cell to the biocathode (40) of another biofuel cell, which is in turn connected to another bioanode (41) until the desired stack is obtained. Fuel fluid and/or oxidant flows into the microfluidic chamber in an entry reservoir (33). By forming stacks, the total voltage output of a microfluidic biofuel cell circuit is theoretically the sum of the voltage output from the individual microfluidic biofuel cells in series. The greater overall voltage output of such a stack is useful in supplying electricity to electronic devices, toys, medical devices, and vehicles with power requirements higher than an individual microfluidic biofuel cell could provide.

IV. Methods of Generating Electricity

The invention includes a method of generating electricity comprising oxidizing the fuel fluid at the anode and reducing the oxidant at the cathode, wherein the electricity is generated using a biofuel cell comprising the bioanodes and/or biocathodes as described above.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "acyl," as used herein alone or as part of another group, denotes the moiety formed by removal of the hydroxyl group from the group —COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The term "heteroatom" shall mean atoms other than carbon and hydrogen. The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The following examples illustrate the invention.

EXAMPLES

Example 1

Direct Electron Transfer Using Bilirubin Oxidase on Different Carbon Surfaces

Carbon Paste Electrode Modifications: Each experiment was conducted using freshly packed carbon paste electrodes. Following carbon paste packing, the four electrodes were modified with one of the carbon materials: carbon black, carbon worms, carbon nanotubes with a diameter of 20 nm and a length of 5-20 microns, and Pt on Vulcan XC-72. Unmodified carbon paste electrodes were used as a control. Modified electrodes were soaked in a solution of bilirubin oxidase in a pH 7.15 pH buffer solution for 15 minutes at 4° C. The bilirubin oxidase enzyme solution contained 1.0 mg of bilirubin oxidase dissolved in 10 mL of the 0.1 M pH 7.15 phosphate buffer. Once the electrodes equilibrated in the enzyme solution, they were placed in a vacuum desiccator to dry for approximately 15 minutes. Once dry, the electrodes were voltammetrically tested in a control solution of degassed pH 7.15 phosphate buffer solution. The modified carbon paste electrodes were used as the working electrode then coupled with a platinum mesh counter electrode and a SCE reference electrode. Each electrode was scanned from 0.8V to –0.1V at a scan rate of 0.01 V/s. After testing each modified carbon paste electrode in the degassed phosphate buffer, the test solution was oxygenated and each electrode was scanned using the same parameters as described earlier in order to determine if direct electron transfer had occurred.

These studies resulted in the data presented in the following table. These data show that electrode modification with carbon nanotubes results in the greatest flux enhancement.

TABLE

Flux Enhancement for bilirubin oxides adsorbed on modified carbon paste electrodes in buffer

| Electrode Modifier | Flux Enhancement |
|---|---|
| Carbon black | 4.88 ± 1.88 |
| Expanded graphite worms | 1.81 ± 0.67 |
| Pt on Vulcan XC-72 | 4.03 ± 0.58 |
| Carbon nanotubes | 14.12 ± 3.17 |
| Carbon paste | 2.46 ± 0.82 |

Three separate methods were employed to make TBAB modified Nafion®/carbon nanotube composites. The first method (Method 1) involved polishing glassy carbon electrodes on Buehler cloths using 0.1 µm alumina followed by a methanol and water rinse to ensure no prior electrode fouling. A carbon nanotube slurry was prepared using 0.05 g of nanotubes combined with the bilirubin oxidase solution prepared as previously described. This paste was allowed to dry until it formed a damp paste. The carbon paste was then placed in a vacuum desiccator and allowed to completely dry. Next, 2.0 mg of the dried paste was combined with 100 µL of the TBAB modified Nafion® polymer in solution. The suspension was vortexed in a Scientific Industries Vortex Genie 2 to ensue proper mixing. Twenty microliters of the suspension was pipetted onto the tip of a polished glassy carbon electrode (GCE). The modified electrodes were spin coated at speeds varying from 10 to 50 rpm then placed in a vacuum desiccator and allowed to dry for approximately 15 minutes. The spin coated TBAB modified Nafion® with enzyme/nanotube paste in suspension were tested in the same manner as previously described, in a degassed pH 7.15 buffer solution using a SCE reference electrode and platinum mesh as the counting electrode. Each electrode was scanned from 0.8V to –0.1V at a scan rate of 0.01 V/s using a cyclic voltammetry. Following the control experiments the pH 7.15 phosphate buffer solution was oxygenated for at least 15 minutes prior to sample experiments being run. All data from these experiments were interfaced and recorded using a CH Instruments potentiostat interfaced to a PC.

The second method (Method 2) involved polishing glassy carbon electrodes as described above. A nanotube and bilirubin oxidase paste was made by containing 0.05 grams of nanotubes suspended in 1.0 mL of the bilirubin oxidase solution prepared as described. The enzyme/nanotube suspension was vortexed in a Scientific Industries Vortex Genie 2 in order to ensure proper mixing. Twenty microliters of the suspension was pipetted onto the tip of a polished glassy carbon electrode. Electrodes were dried in a vacuum desiccator for approximately 15 minutes. Following drying, 5 µL of TBAB modified Nafion® was spin-coated over the nanotubes/bilirubin oxidase paste modified electrode. The spin coated electrodes were then dried in a vacuum desiccator for approximately 15 minutes. The enzyme/nanotube paste spin coated with TBAB modified Nafion® electrodes were tested in the same manner as described.

The third method (Method 3) again began with polishing glassy carbon electrodes. Then, a nanotube paste was made containing 0.05 grams of nanotubes suspended in 1.0 mL of pH 7.15 phosphate buffer. The nanotube suspension was vortexed in a Scientific Industries Vortex Genie 2 in order to ensure proper mixing. Twenty microliters of the nanotube suspension was pipetted onto the tip of the electrode over the dried nanotube paste then allowed to dry in a vacuum desiccator for approximately 15 minutes. Twenty microliters of the bilirubin oxidase enzyme solution prepared as described above was pipetted onto the tip of the electrode over the dried nanotube paste. Once dry, these electrodes were spin-coated with 5 µl of the TBAB modified Nafion® polymer at 50 rpm. The electrodes were allowed to dry in a vacuum desiccator for approximately 15 minutes. The nanotube paste/enzyme solution coated spin coated with TBAB modified Nafion® electrodes were tested in the same manner as previously described.

Results of these experiments are tabulated below. These data show that Method 1 is the preferred method for forming carbon nanotube/enzyme/TBAB modified Nafion® composites as it provides significant flux enhancement with less variability than Method 2.

TABLE 2

Comparison of the flux enhancements for difference methods of forming carbon nanotube/enzyme/TBAB modified Nafion ® composites

| Nanotube/enzyme/TBAB modified Nafion ® composite | Flux enhancement |
|---|---|
| Method 1 | 27.1 ± 7.9 |
| Method 2 | 35.8 ± 20.1 |
| Method 3 | 16.8 ± 6.7 |

Example 2

Bilirubin Oxidase Cathodes in Biofuel Cells

The anode and the cathode electrodes in the biofuel cell were prepared using biological catalysts (enzymes). A tetrabutylammonium-modified Nafion® NAD+-dependent alcohol dehydrogenase bioanode was used for these experiments. A biocathode was developed that consists of 1 cm² carbon cloth. 0.5 mg bilirubin oxidase (from Myrothecium verrucaria, unit activity=10 units.mg, Sigma) was added to 100 µL of DE 520 Nafion membrane suspension and vortexed for 20 minutes. Two microliters of enzyme/membrane casting solution were pipetted onto the carbon electrode and allowed to dry for 12 hours. All electrochemical experiments were performed at room temperature, which varied from 20-25° C. Electrodes were introduced into pH=7.15, 7.5 and 8.0 phosphate buffers saturated with dissolved oxygen. The measurements were conducted on a CH Instrument potentiostat model 900 interfaced to a PC computer. The DE520 Nafion® membrane suspension was prepared by adding 0.09672 g TBAB (tetrabutylammonium bromide) to 1 mL DE520 Nafion. The mixture solution was then cast in a weigh boat and allowed to dry overnight. Once dry, the mixture-cast film was soaked in 18 MΩ water for 24 hours to remove all excess bromide salts. After the salts extraction, the films were thoroughly rinsed with 18 MΩ water three times and allowed to dry. The film was resuspended in 1 mL ethanol.

Two types of electrochemical cells were used. The traditional fuel cell was tested in a U-shaped glass cell where the anode and cathode compartment were separated by Nafion® 117 PEM membrane (Alfa Aesar). For the second type of fuel cell (the membraneless fuel cell), the biocathode and bioanode were introduced into 50 mL beaker containing the fuel solution. The fuel solution consisted of 1.0 mM ethanol and 1.0 mM NAD+ in phosphate buffer of pH 7.15, 7.5 and 8.0. The solution is allowed to equilibrate in air to ensure dissolved oxygen in the buffer before testing. The electrodes were positioned approximately 1 cm apart to ensure that they did not come into contact with each other.

The traditional fuel cell was tested in a U-shaped glass cell where the anode and cathode compartment were separated by a Nafion® 117 PEM membrane (Alfa Aesar). The anolytes were 1.0 mM fuel solutions in phosphate buffers of different pHs, while the catholytes were buffer solutions with different pHs exposed to air. During the experiments, the only source of oxygen was the dissolved oxygen in the buffer. The completed NAD+-dependent bioanode was introduced into a separate anodic fuel cell chamber coupled to its own cathodic chamber containing a bilirubin oxidase biocathode.

The membraneless ethanol/oxygen biofuel cell was formed by placing the biocathode and bioanode in a beaker containing 1.0 mM NAD+ and 1.0 mM ethanol in pH 8.0 buffer solutions that had been exposed to air. During normal testing of the previously developed bioanode, NAD+ is not added to the buffer solution because NAD+ is electrostatically immobilized within the bioanode. However, NAD+ was added to the solution for testing this system to ensure that any NAD+ that might leach from the bioanode would not affect the biocathode reactions or biocathode lifetime. The initial open circuit potential of the membraneless biofuel cell was 1.20 V and the maximum power density was 0.64 mW/cm². It can be noted that both the open circuit potentials and the power densities are higher for the membraneless system. The increase for the biofuel cell wherein the bilirubin oxidase biocathode does not contain a redox mediator as compared to the biofuel cell containing a bilirubin oxidase biocathode that does contain redox mediator is 0.30 V for the open circuit potential and 0.25 mW/cm² for the power density.

Table 3 compares the data obtained using different biofuel cells at room temperature and different buffer pHs. It can be observed that using traditional biofuel cells with increasing solution pH, the open circuit potential, current densities and power densities are also increasing. A maximum open circuit potential of 1.16 V with 7.65 mA/cm² current density and 0.45 mW/cm² power density at pH 8.0 was obtained. For a membraneless biofuel cell, in the same work conditions, a maximum open circuit potential of 1.10 V with 11.7 mA/cm² current density and 0.64 mW/cm² power density, at pH 8.0 was obtained. A higher open circuit potential, 1.20 V, at pH 7.15 was obtained, but at this pH the current and power density are lower than at pH 8. It can be concluded that for membraneless biofuel cells, an increase in fuel solution pH leads to a small decrease in open circuit potentials and an increase in currents and power densities.

TABLE 3

| Fuel Cells | Results | | |
| --- | --- | --- | --- |
| | Maximum Open Circuit Potential (V) | Maximum Current Density (mA/cm²) | Maximum Power Density (mW/cm²) |
| Traditional cell pH = 7.15 | 0.90 | 3.40 | 0.17 |
| Traditional cell pH = 7.50 | 1.05 | 4.20 | 0.21 |
| Traditional cell pH = 8.00 | 1.16 | 7.65 | 0.45 |
| Membraneless cell pH = 7.15 | 1.20 | 7.70 | 0.38 |
| Membraneless cell pH = 7.50 | 1.15 | 7.40 | 0.37 |
| Membraneless cell pH = 8.00 | 1.10 | 11.7 | 0.67 |

Figure 6:
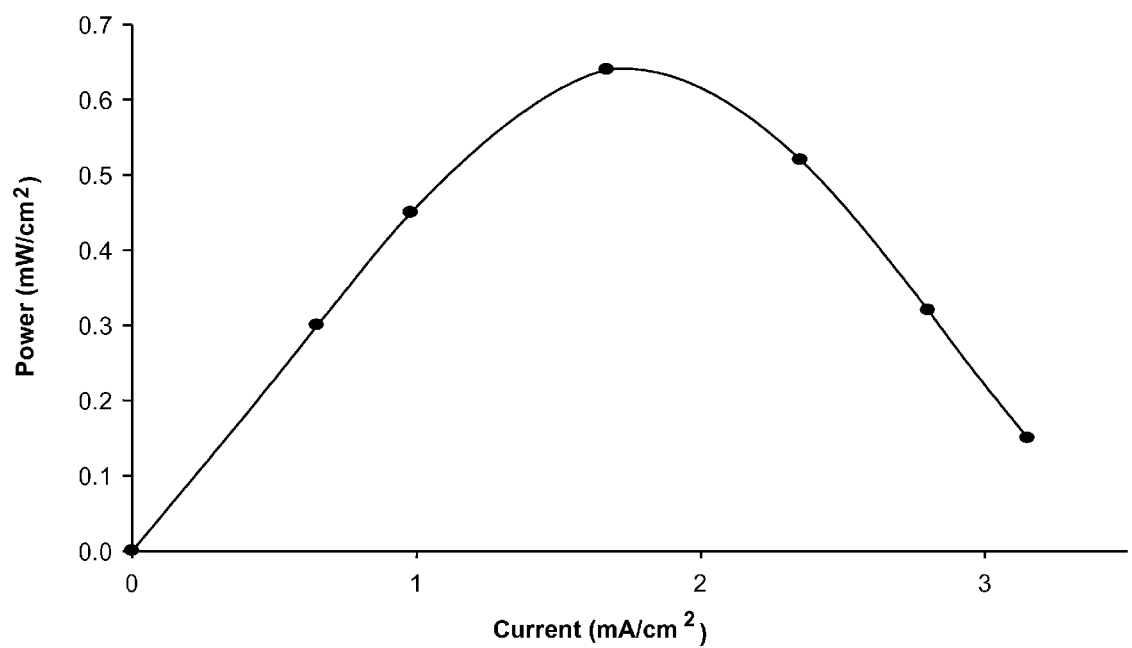
FIG. 6 is a power curve for a membraneless biofuel cell having a mediated bioanode (comprising tetrabutylammonium-modified Nafion® and NAD+-dependent alcohol dehydrogenase) and a direct electron transfer biocathode (comprising tetrabutylammonium-modified Nafion® and bilirubin oxidase).
Figure 7:
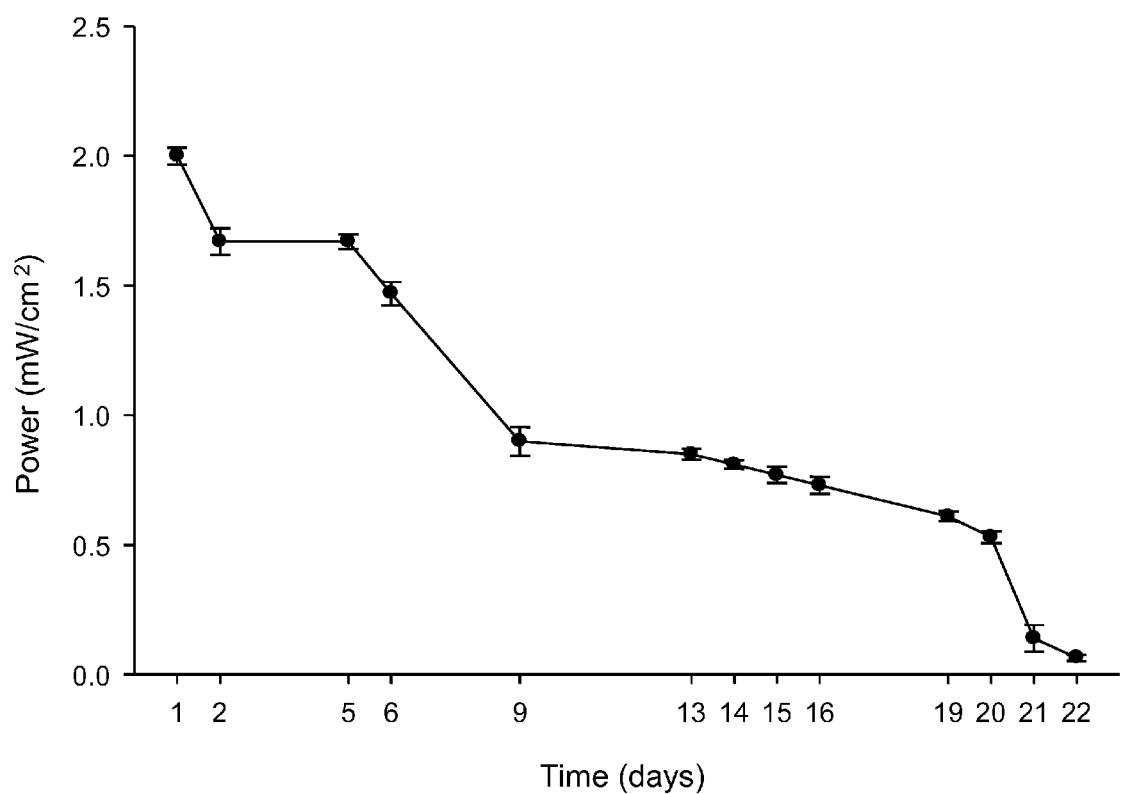
FIG. 7 is a graph showing the power of a membraneless biofuel cell having a mediated bioanode (comprising tetrabutylammonium-modified Nafion® and $NAD^+$-dependent alcohol dehydrogenase) and a direct electron transfer biocathode (comprising tetrabutylammonium-modified Nafion® and bilirubin oxidase) as a function of time.
Figure 8:
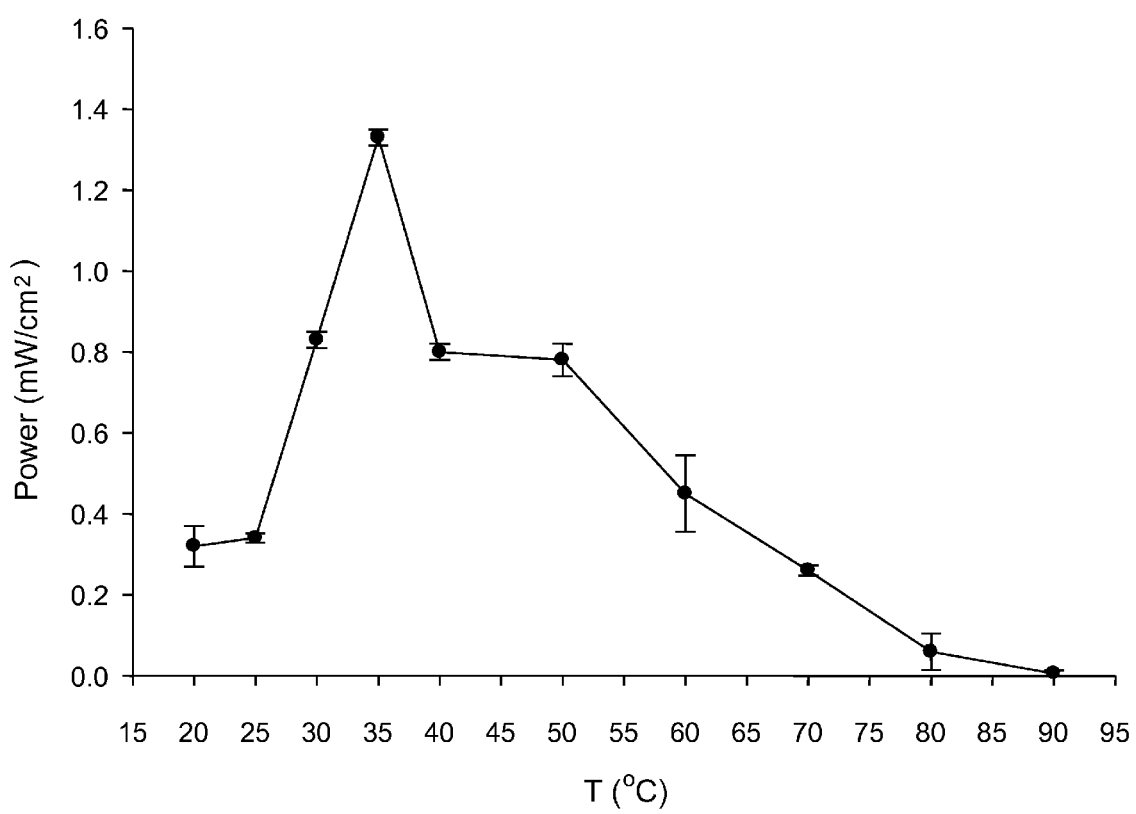
FIG. 8 is a graph showing the power of a membraneless biofuel cell having a mediated bioanode (comprising tetrabutylammonium-modified Nafion® and $NAD^+$-dependent alcohol dehydrogenase) and a direct electron transfer biocathode (comprising tetrabutylammonium-modified Nafion® and bilirubin oxidase) as a function of temperature.

Further experimental results for the membraneless biofuel cell described above were collected at room temperature in a 1.0 mM NAD+ solution in pH 8.0 phosphate buffer. FIG. 6 shows a representative power curve for this system. FIG. 7 shows the power output for this system as a function of time from fabrication. FIG. 8 shows the power output as a function of temperature at 50% humidity. The following table details the maximum open circuit potential, maximum current density and maximum power density at varying ethanol concentrations.

| Ethanol Concentration (mM) | Maximum Open Circuit Potential (V) | Maximum Current Density (mA/cm²) | Maximum Power Density (mW/cm²) |
| --- | --- | --- | --- |
| 1 | 1.10 | 11.70 | 0.67 |
| 10 | 1.03 | 10.78 | 0.31 |
| 100 | 1.05 | 11.60 | 0.20 |
| 500 | 1.08 | 6.53 | 0.17 |
| 1000 | 0.99 | 6.78 | 0.08 |

Example 3

Preparation of Lipoxygenase Bioanode

Suspensions of various ammonium salt-treated Nafion® enzyme immobilization materials were prepared as described above. A stock solution of lipoxygenase enzyme was prepared. An equal amount of the lipoxygenase solution and modified Nafion® suspension was mixed and the solution was pipetted onto the surface of a 1 cm² carbon paper support and dried thoroughly.

A U-shaped glass cell with Nafion™ 117 membrane separating the anode and cathode compartment was utilized. The cathode side of the fuel cell was filled with buffer (pH ~7.15) and a platinum cathode was partially suspended in solution. The anode side of the fuel cell was filled with sonicated fuel solution containing 10 µL of soybean oil in 100 mL of buffer. The anode was suspended completely into the solution. The Nafion® was modified with tetrabutylammonium bromide (TBAB), triethylhexylammonium bromide (TEHA), trimethylhexylammonium bromide (TMHA), trimethyloctylammonium bromide (TMOA), trimethyldecylammonium bromide (TMDA), trimethyldodecylammonium bromide (TMDDA), or trimethyltetradecylammonium bromide (TMTDA). The following table details the results of various bioanodes containing the modified Nafion® membranes and lipoxygenase enzymes.

was pipetted onto the polymer cast and allowed to soak for two minutes. After soaking, the slides were rinsed with 18 MΩ water and allowed to dry in the desiccator. The polymers were imaged using an Olympus BX60M epifluorescence microscope (Melville, N.Y.). The polymers were observed under a 40× ultra-long working distance lens with a video camera (Sony SSC-DC50A). Fluorescence excitation was achieved with a mercury lamp. A frame grabber card (Integral Technologies, Inc., Indianapolis, Ind.) was used to acquire images, and the images were analyzed using SPOT software (Diagnostic Instruments, Inc.) on a Dell PC. Fluorescence imaging of each of the hydrophobically modified polyelectrolytes in $Ru(bpy)_3^{+2}$ and fluorescein was performed to determine the morphological effects of the hydrophobic modification. Fluorescence studies showed that aggregates formed within the hydrophobically modified chitosans and that the morphology changed with alkyl chain length. The butyl modified chitosan appeared to have small, fibrous interconnects, whereas the hexyl modified chitosan had large domains containing smaller micellar domains. As the alkyl chain length increased, the number of micellar domains decreased, but the size of the domain increased. Fluorescence micrographs of unmodified chitosan did not show distinct domains, so micellar structure was not observed for unmodified chitosan.

|  | TBAB | TEHA | TMHA | TMOA | TMDA | TMDDA | TMTDA |
|---|---|---|---|---|---|---|---|
| Best Open Circuit Potential (V) | 0.96 | 0.91 | 0.90 | 0.91 | 0.91 | 0.97 | 0.96 |
| Maximum Current (mA/cm²) | 7.67 | 9.18 | 9.53 | 8.23 | 9.23 | 10.6 | 8.83 |
| Maximum Power (mW/Cm²) | 3.78 | 3.85 | 3.89 | 3.54 | 3.95 | 4.39 | 4.14 |
| Maximum Lifetime | 1+ year | 1+ year | 1+ year | 1+ year | 1+ year | 1+ year | 1+ year |

Example 4

Preparation of Alkyl Modified Chitosan

Medium molecular weight chitosan (available from Aldrich) (0.500 g) was dissolved by rapid stirring in 15 mL of 1% acetic acid. This resulted in a viscous gel-like solution and then 15 mL of methanol was added. The chitosan gel was allowed to stir for approximately 15 minutes, then 20 mL aldehyde (butanal, hexanal, octanal, or decanal) was added to the chitosan gel, followed by 1.25 g of sodium cyanoborohydride. The gel was continuously stirred until the suspension cooled to room temperature. The resulting product was separated by vacuum filtration and washed with 150 mL increments of methanol three times. The modified chitosan was then dried in a vacuum oven at 40° C. for two hours, leaving a flaky white solid. One percent by weight suspensions of each of the polymers were formed in 50% acetic acid, chloroform, and t-amyl alcohol.

Example 5

Fluorescence Imaging of Hydrophobically Modified Chitosans

Two microliters of each polymer suspension were cast onto a glass microscope slide (Fisher) and dried in the desiccator. A 20 µL volume of 0.01 mM $Ru(bpy)_3^{2+}$ or 0.01 mM FITC

Example 6

Electrochemical Measurements of Hydrophobically Modified Chitosans

Glassy carbon working electrodes (3 mm in diameter, CH Instruments) were polished on a Buehler polishing cloth with 0.05 micron alumina and rinsed in 18 MΩ water. Two microliters of each polymer suspension was cast onto a glassy carbon electrode surface and allowed to dry in a vacuum desiccator until use. Cyclic voltammetry was used to measure the flux of the redox species through the polymer membrane at the electrode surface. The working electrodes were allowed to equilibrate in a 1.0 mM redox species solution containing 0.1 M sodium sulfate as the supporting electrolyte along with a platinum mesh counter electrode and measured against a saturated calomel reference electrode. The redox species studied were caffeine, potassium ferricyanide, and $Ru(bpy)_3^{2+}$. The data were collected and analyzed on a Dell computer interfaced to a CH Instruments potentiostat model 810. Cyclic voltammetry was performed at scan rates ranging from 0.05 V/s to 0.20 V/s. All experiments were performed in triplicate and reported uncertainties correspond to one standard deviation.

Cyclic voltammetric studies of the two hydrophobically modified polyelectrolytes were conducted as a function of the alkyl chain length of the hydrophobic modification. All cyclic voltammetric experiments showed linear $i_p$ vs $v^{1/2}$ plots, signifying transport-limited electrochemistry. Since electrochemical flux is a function of concentration as shown in Equation 2, $KD^{1/2}$ values are reported herein as a concentration independent method of comparing fluxes.

$$\text{Flux} = \frac{i}{nFA} = \frac{2.69 \times 10^5 n^{3/2} AC* v^{1/2} KD^{1/2}}{nFA} \quad \text{Equation 2}$$

where i is the peak current, n is the number of electrons transferred, F is Faraday's constant, A is the area of the electrode, C* is the concentration of redox species, v is the scan rate, K is the extraction coefficient, and D is the diffusion coefficient. The solvent determines the degree of swelling of the polymer during re-casting. Most literature studies on chitosan and chitosan derivatives employ acetic acid as the solvent for resuspension, however, it is important to note from the $KD^{1/2}$ values, chloroform provides a higher average flux. Unmodified chitosan is only soluble in the acetic acid solution. The $KD^{1/2}$ value for unmodified chitosan in caffeine is 5.52 ($\pm$0.14)$\times 10^{-3}$. It is clear that hydrophobic modification of chitosan can decrease the flux of caffeine, but cannot make appreciable increases in flux.

On the other hand, transport of large, hydrophobic ions, like $Ru(bpy)_3^{+2}$, can be greatly affected by small changes in pore structure/size. The $KD^{1/2}$ value for $Ru(bpy)_3^{+2}$ transport through unmodified chitosan is 2.17 (+0.33)$\times 10^{-4}$. It is evident that hydrophobic modification of chitosan increased the transport of $Ru(bpy)_3^{+2}$ in all cases, by as much as 11.1 fold for octyl modified chitosan membrane resuspended in t-amyl alcohol.

Example 7

Preparation of Electrodes

A solution of 2 wt. % of a hydrophobically modified chitosan polymer was suspended in t-amyl alcohol and a solution of glucose oxidase was added. This solution was pipeted onto an electrode material. This electrode material was typically a carbon cloth, or other carbon material.

Example 8

Glucose Oxidase Activity Tests for Hydrophobically Modified Chitosans

Glucose oxidase (GOx) catalyzes the oxidation of β-D-glucose to D-glucono-δ-lactone with the concurrent release of hydrogen peroxide. It is highly specific for β-D-glucose and does not act on α-D-glucose. In the presence of peroxidase, hydrogen peroxide enters into a second reaction in the assay involving p-hydroxybenzoic acid and 4-amino antipyrine with the quantitative formation of quinoneimine dye complex, which is measured at 510 nm. The activity of GOx enzyme was measured in each of the hydrophobically modified Nafion and chitosan membranes. The absorbance was measured at 510 nm against water after immobilizing the GOx enzyme within the hydrophobically modified chitosan membranes, and casting it in a plastic vial. All experiments were performed in triplicate and reported uncertainties correspond to one standard deviation.

As described above and tabulated in Table 2, the highest enzyme activity was observed for glucose oxidase in a hexyl modified chitosan suspended in t-amyl alcohol. These immobilization membranes showed a 2.53 fold increase in GOx enzyme activity over enzyme in buffer.

Example 9

Chitosan-Butyl Biocathodes

Figure 9:
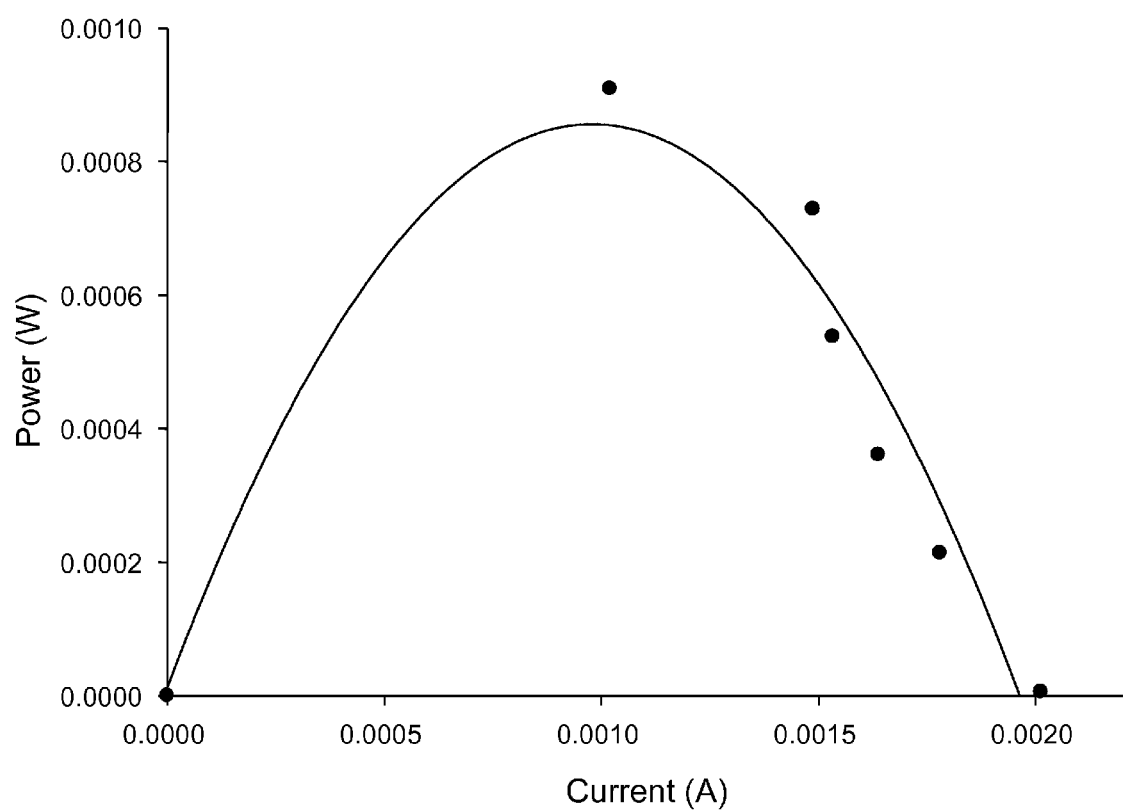
FIG. 9 is a power curve for a biofuel cell having a mediated bioanode (comprising tetrabutylammonium-modified Nafion® and $NAD^+$-dependent alcohol dehydrogenase) and a direct electron transfer biocathode (comprising butyl-chitosan and bilirubin oxidase).
Figure 10:
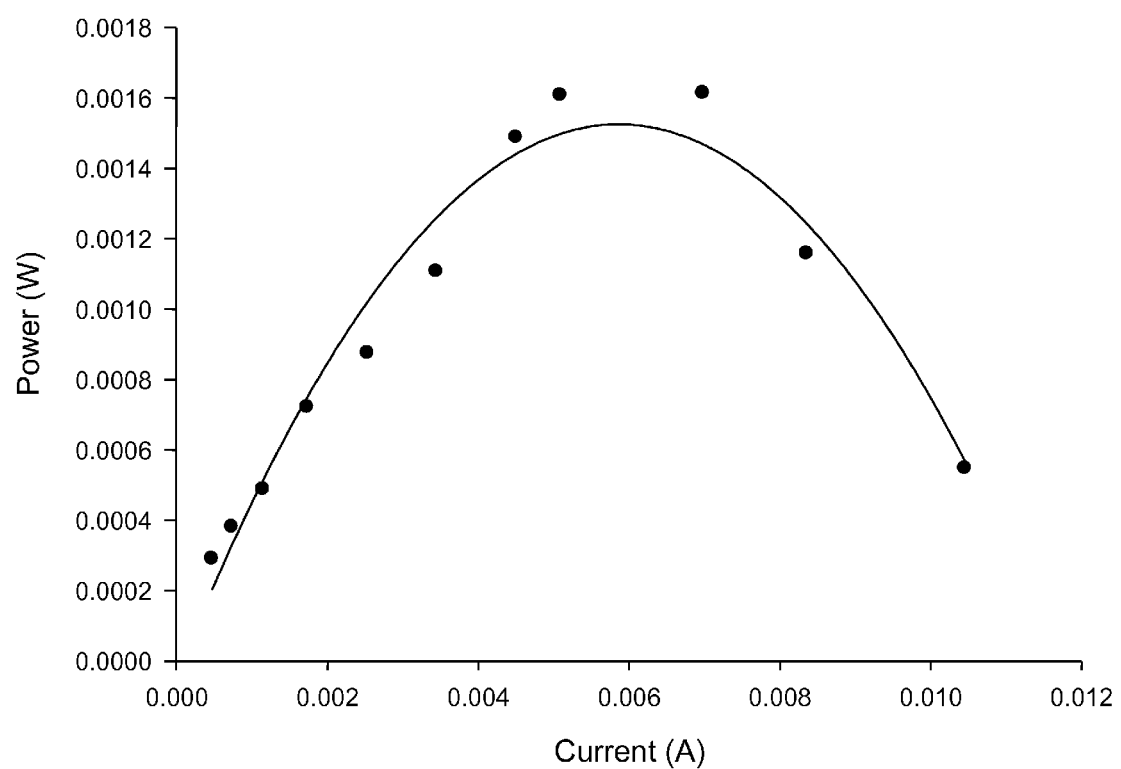
FIG. 10 is a power curve for a biofuel cell having a mediated bioanode (comprising butyl-chitosan and $NAD^+$-dependent alcohol dehydrogenase) and a direct electron transfer biocathode (comprising butyl-chitosan and bilirubin oxidase).

Bilirubin Oxidase. Chitosan mixtures were prepared by mixing 0.01 g hydrophobically modified chitosan (butyl, hexyl, octyl or decyl) with 1 mL Nafion® DE 520 and vortexing with mixing beads for 1 hour. A 40 μL aliquot of the chitosan/Nafion® mixture was then mixed with a 20 μL aliquot of bilirubin oxidase (1 mg enzyme in 10 mL pH 7.15 phosphate buffer) for 1 minute. The chitosan/enzyme mixture was pipetted onto a 1 $cm^2$ piece of carbon paper to fabricate the cathode and it was allowed to completely dry in the vacuum dessicator. Data for power curves were collected for a butyl-chitosan bilirubin oxidase cathode combined with either (1) a TBA-modified Nafion® $NAD^+$-dependent alcohol dehydrogenase anode (FIG. 9) or (2) butyl-chitosan $NAD^+$-dependent alcohol dehydrogenase anode (FIG. 10)

Also, a study to determine the optimum temperature for operation of various biofuel cells was undertaken. The maximum open circuit potential (V), maximum current density (mA/$cm^2$) and maximum power density (mW/$cm^2$) for (1) a TBA-modified Nafion® $NAD^+$-dependent alcohol dehydrogenase anode and a butyl-chitosan bilirubin oxidase cathode, (2) a butyl-chitosan $NAD^+$-dependent alcohol dehydrogenase anode and a TBA-modified Nafion® bilirubin oxidase cathode, and (3) a butyl-chitosan $NAD^+$-dependent alcohol dehydrogenase anode and a butyl-chitosan bilirubin oxidase cathode were measured at various temperatures. This temperature data is presented in the following tables.

TABLE

Mediated bioanode (comprising TBA-modified Nafion ® and $NAD^+$-dependent alcohol dehydrogenase) and a direct electron transfer biocathode (comprising butyl-chitosan and bilirubin oxidase)

| | Results | | |
|---|---|---|---|
| Temperature (° C.) | Maximum Open Circuit Potential (V) | Maximum Current Density (mA/$cm^2$) | Maximum Power Density (mW/$cm^2$) |
| 20 | 1.113 | 8.27e-4 | 8.38e-4 |
| 25 | 1.118 | 1.24e-3 | 1.26e-3 |
| 30 | 1.126 | 1.29e-3 | 1.33e-3 |
| 35 | 1.092 | 6.90e-4 | 6.85e-4 |
| 40 | 1.090 | 9.45e-4 | 9.35e-4 |
| 50 | 1.093 | 1.38e-3 | 1.38e-3 |
| 60 | 1.070 | 1.22e-3 | 1.19e-3 |
| 70 | 0.558 | 3.11e-4 | 1.43e-4 |
| 80 | 0.347 | 9.46e-5 | 2.34e-5 |
| 90 | 0.122 | 2.43e-5 | 5.34e-7 |

TABLE

Mediated bioanode (comprising butyl-chitosan and $NAD^+$-dependent alcohol dehydrogenase) and a direct electron transfer biocathode (comprising TBA-modified Nafion ® and bilirubin oxidase)

| | Results | | |
|---|---|---|---|
| Temperature (° C.) | Maximum Open Circuit Potential (V) | Maximum Current Density (mA/$cm^2$) | Maximum Power Density (mW/$cm^2$) |
| 20 | 0.8078 | 2.69e-4 | 1.90e-4 |
| 25 | 0.8648 | 5.00e-4 | 3.82e-4 |

TABLE-continued

Mediated bioanode (comprising butyl-chitosan and NAD⁺-dependent alcohol dehydrogenase) and a direct electron transfer biocathode (comprising TBA-modified Nafion ® and bilirubin oxidase)

| | Results | | |
|---|---|---|---|
| Temperature (° C.) | Maximum Open Circuit Potential (V) | Maximum Current Density (mA/cm$^2$) | Maximum Power Density (mW/cm$^2$) |
| 30 | 0.8809 | 6.00e−4 | 4.68e−4 |
| 35 | 0.8896 | 6.54e−4 | 5.76e−4 |
| 40 | 0.8880 | 7.43e−4 | 5.86e−4 |
| 50 | 0.8999 | 9.81e−4 | 7.85e−4 |
| 60 | 0.9100 | 1.021e−4 | 8.27e−4 |
| 70 | 0.804 | 3.80e−4 | 2.66e−4 |
| 80 | 0.489 | 1.81e−4 | 6.78e−5 |
| 90 | 0.1963 | 7.23e−5 | 6.93e−6 |

TABLE

Mediated bioanode (comprising butyl-chitosan and NAD⁺-dependent alcohol dehydrogenase) and a direct electron transfer biocathode (comprising butyl-chitosan and bilirubin oxidase)

| | Results | | |
|---|---|---|---|
| Temperature (° C.) | Maximum Open Circuit Potential (V) | Maximum Current Density (mA/cm$^2$) | Maximum Power Density (mW/cm$^2$) |
| 20 | 0.9243 | 2.94e−4 | 2.42e−4 |
| 25 | 0.9871 | 4.77e−4 | 4.24e−4 |
| 30 | 0.9600 | 6.12e−4 | 5.27e−4 |
| 35 | 0.9680 | 7.00e−4 | 6.02e−4 |
| 40 | 0.9702 | 8.37e−4 | 7.30e−4 |
| 50 | 0.9480 | 6.13e−4 | 5.20e−4 |
| 60 | 0.9430 | 5.57e−4 | 4.69e−4 |
| 70 | 0.5972 | 2.38e−4 | 1.19e−4 |
| 80 | 0.2796 | 9.46e−5 | 1.70e−5 |
| 90 | 0.1038 | 3.49e−5 | 1.32e−7 |

Example 10

Preparation of Alkyl Modified Alginate

Alginate membranes incorporated with quaternary ammonium bromides were formed by co-casting the quaternary ammonium bromide with 3 wt. % alginate suspension. The polymer used was either ultra low, low, or medium molecular weight alginate. The mixture-casting solutions were prepared by adding the quaternary ammonium bromides to the 3 wt. % suspension. All mixture-casting solutions were prepared so the concentration of quaternary ammonium bromides is in excess of the concentration of carboxylic acid sites in the alginate suspension. After optimization, it was determined that the most stable and reproducible membrane has a quaternary ammonium bromide concentration that is three times the concentration of the exchange sites.

One milliliter of the casting solution was placed in a weighing boat and allowed to dry. 7.0 mL of 18 MΩ water were added to the weighing boats and allowed to soak overnight. The water was removed and the films were rinsed thoroughly with 18 MΩ water and dried. Then, the films were resuspended in 1.0 mL of methanol. Ammonium bromide salts of tetrapropylammonium (T3A), tetrapentylammonium (T5A), tetrahexylammonium (T6A), tetraheptylammonium (T7A), trimethylicosylammonium (TMICA), trimethyloctyldecylammonium (TMODA), trimethylhexyldecylammonium (TMHDA), trimethyltetradecylammonium (TMTDA), trimethyloctylammonium (TMOA), trimethyldodecylammonium (TMDDA), trimethyldecylammonium (TMDA), trimethylhexylammonium (TMHA), tetrabutylammonium (TBA), and triethylhexylammonium (TEHA) were used as alginate modifiers to see which yielded the best micellar structure. The micellar structure is important for effective immobilization of an enzyme.

To determine the pore characteristics, three drops of each polymer were then placed on a slide and left to dry. After completely drying, they were soaked in 1 mM Ru(bpy)$_3^{+2}$ in ethanol for at least 3 hours. After being rinsed off with ethanol, the polymers were left to dry before being imaged with a fluorescence microscope to see the micellar structure. An example of the structure is shown in FIG. 11.

In another experiment, ultralow molecular weight alginate and dodecylamine were placed in 25% ethanol and refluxed to produce a dodecyl-modified alginate by amidation of the carboxylic acid groups.

Example 11

Preparation of Alginate Electrodes

A solution of 3 wt. % of an alginate polymer modified with a hydrophobic ammonium cation described in Example 10 is suspended in alcohol and a solution of enzyme (e.g., bilirubin oxidase) is added. This solution is pipeted onto an electrode material. This electrode material is typically a carbon cloth, or other carbon material.

Example 12

Alginate Biofuel Cells

A biofuel cell having an anode enzyme immobilized in a hydrophobically modified alginate is prepared by mixture casting a hydrophobically modified alginate with a solution of enzyme and buffer and pipeting the mixture on a carbon cloth, thus, forming a bioanode similar to those described above in Example 10. A biocathode comprising a hydrophobically modified Nafion® membrane as described above and in U.S. patent application Ser. No. 10/931,147 (published as U.S. Patent Application Publication No. 2005/0095466) can be used to form a biofuel cell having a bioanode and a biocathode. Alternatively, a biofuel cell having a cathode enzyme immobilized in a hydrophobically modified alginate is prepared by mixture casting a hydrophobically modified alginate with a solution of enzyme and buffer and pipeting the mixture on a carbon cloth, thus, forming a biocathode. A bioanode comprising a hydrophobically modified Nafion® membrane as described above and in U.S. patent application Ser. No. 10/617,452 (published as U.S. Patent Application Publication No. 2004/0101741) can be used to form a biofuel cell having a bioanode and a biocathode. In another embodiment, a biofuel cell can be prepared that has a cathode enzyme immobilized in a hydrophobically modified alginate prepared as described above and a bioanode having an anode enzyme immobilized in a hydrophobically modified alginate prepared as described above.

Example 13

Biofuel Cell

A biofuel cell having an anode enzyme immobilized in a hydrophobically modified chitosan is prepared by mixture casting a hydrophobically modified chitosan with a solution of enzyme and buffer and pipeting the mixture on a carbon cloth, thus, forming a bioanode. A biocathode comprising a hydrophobically modified Nafion® membrane as described in U.S. patent application Ser. No. 10/931,147 (published as U.S. Patent Application Publication No. 2005/0095466) can be used to form a biofuel cell having a bioanode and a biocathode. Alternatively, a biofuel cell having a cathode enzyme immobilized in a hydrophobically modified chitosan is prepared by mixture casting a hydrophobically modified chitosan with a solution of enzyme and buffer and pipeting the mixture on a carbon cloth, thus, forming a biocathode. A bioanode comprising a hydrophobically modified Nafion® membrane as described in U.S. patent application Ser. No. 10/617,452 (published as U.S. Patent Application Publication No. 2004/0101741) can be used to form a biofuel cell having a bioanode and a biocathode. A bioanode having an anode enzyme immobilized in a hydrophobically modified chitosan is prepared by mixture casting a hydrophobically modified chitosan with a solution of enzyme and buffer and pipeting the mixture on a carbon cloth, thus, forming a bioanode for use in the biofuel cell.

Example 14

Microfluidic Biofuel Cell

Masters for the production of PDMS micromolding channels are made by coating a 4-in. silicon wafer with SU-8 10 negative photoresist using a spin coater (Brewer Science, Rolla, Mo.) operating with a spin program of 1000 rpm for 30 seconds for micromolding channel. For flow channels, a spin program of 1750 rpm for 30 seconds is used with SU-8 50 negative photoresist. The photoresist is prebaked at 90° C. for 5 minutes prior to UV exposure for 4 minutes with a near-UV flood source (Autoflood 1000, Optical Associates, Milpitas, Calif.) through a negative film containing the micromolding channel or flow channel design structures (Jostens, Topeka, Kans.). The transparency is made from a computer design drawn in Freehand (PC Version 8.0, Macromedia Inc., San Francisco, Calif.). The design is transferred to a transparency using an image setter with a resolution of 2400 dpi by a printing service (Jostens, Topeka, Kans.). Following this exposure, the wafer is postbaked at 90° C. for 5 minutes and developed in Nano SU-8 developer. The wafers containing the desired design are rinsed with acetone and isopropanol in order to remove any excess, unexposed photoresist that may have remained on the silicon wafer. The thickness of the photoresist is measured with a profilometer (Alpha Step-200, Tencor Instruments, Mountain View, Calif.), which corresponds to the channel depth of the PDMS structures.

A degassed 10:1 mixture of Sylgard 184 elastomer and curing agent are then poured onto the silicon wafer and cured at 75° C. for approximately 2 hrs. The PDMS is removed from the master wafer by cutting around the edges and peeling back the PDMS from the wafer. The master could be reused in order to generate numerous copies of the PDMS channels. The resulting PDMS flow channel is 200 mm wide, 100 mm deep and 3.0 cm long.

Soda-lime glass plates are purchased from a local glass shop. The plates are 7 cm wide, 10 cm long and 1.54 mm thick. The glass plates are cleaned by soaking them for 15 minutes in piranha solution (70% concentrated $H_2SO_4$/30% $H_2O_2$) to remove organic impurities. Glass is then rinsed thoroughly with Nanopure (18 MΩ-cm) water and dried with nitrogen. Using traditional lithographic and sputtering procedures, palladium electrodes are fabricated on the glass in specific patterns. Each plate could hold several flow channels with electrodes. This is more specifically accomplished by argon ion sputtering of a layer of titanium, for adhesive properties, and a layer of palladium. In order to accomplish this, the glass is placed into a deposition system (Thin Film Deposition System, Kurt J. Lesker Co.) for deposits of the metals. The thickness of the metals is monitored using a quartz crystal deposition monitor (Inficon XTM/2, Leybold Inficon). Titanium is deposited from a Ti-target at a rate of ~2.3 angstroms/s to a depth of 200 angstroms. Palladium is deposited from a Pd-target at a rate of ~1.9 angstroms/s to a depth of 2000 angstroms. AZ 1518 positive photoresist is dynamically dispensed onto the palladium coated glass. A pre-exposure bake at 95° C. for 1 minute is followed by a 9 second ultraviolet exposure through a positive film. The film is removed and the glass placed in a commercially available developer (AZ 300 MIF developer) for 45 seconds. After rinsing with water and drying with nitrogen, the glass is post baked for 1 minute at 95° C. Wet etching is employed using Aqua regia (8:7:1 $H_2O:HCl:HNO_3$) to remove the unwanted palladium and a titanium etchant to remove unwanted titanium from the glass. Once completed, the glass is rinsed with acetone and isopropanol to remove the remaining photoresist and dried with nitrogen.

A flow access hole is drilled through each glass plate, while immersed under water, with a 1-mm diamond drill bit and a Dremel rotary tool (Dremel). The syringe connector portion of a leur adapter is removed with the Dremel rotary tool and accompanying cutting disc. After polishing with a sanding disc, the leur adapter is affixed to the glass plate with J.B. Weld. The epoxy is cured in an oven (75° C.) for 2 hours before use. Connections are made to the palladium electrodes by copper wire and colloidal silver.

To fabricate carbon ink microelectrodes, first the PDMS micromolding channel is sealed to the glass plate in contact with the palladium leads (with leur fitting attached) that had been thoroughly cleaned. The PDMS channels are first primed with solvent thinner (N-160). The thinner is removed by applying a vacuum to one of the reservoirs. As soon as the thinner had been removed, a mixture of commercially available carbon ink and solvent thinner is added to the channels and pulled through the channel by applying vacuum (via water aspirator) to the opposite end. The ink/thinner mixture is made so that the volume of added thinner is 0.2% (v/w) of the initial ink weight. After filling channels with carbon ink, the reservoir where vacuum had been applied is filled with the ink/thinner solution and the entire chip placed in an oven at 75° C. for one hour. After this period of time, the PDMS could be removed from the glass, leaving the carbon microelectrode attached to the glass surface. A final curing/conditioning step is achieved by placing the chip in a separate oven at 12° C. for one hour. The height of the carbon microelectrode is measured with a profilometer and the width is measured via microscopy.

In order to further characterize the carbon ink electrodes, cyclic voltammetry is employed and performed in a 3-electrode format using a CH Instruments 810 bipotentiostat (Austin, Tex.). The carbon microelectrode is the working electrode with a silver/silver chloride reference electrode and a platinum wire as the auxiliary electrode. A static cell for cyclic voltammetry experiments is created in a piece of PDMS by cutting a small section (1 cm×2 cm) out of a larger piece of PDMS (2 cm×3 cm); this piece of PDMS is then sealed over the carbon electrode so the entire length of the electrode is exposed to solution. For flow experiments, a PDMS microchannel (~200 mm wide, 100 mm deep and ~2 cm long) is sealed over the carbon electrode, so the entire electrode is sealed inside the microchannel. The auxiliary and reference electrodes are contained in the outlet reservoir by use of an electrochemical cell holder (CH Instruments).

The flow access hole drilled in the glass plate allows for access to flow from a syringe pump (Pump 11, Harvard Apparatus, Holliston, Mass.). A syringe is filled with the solution of choice and placed in the syringe pump. With the use of high pressure fittings, leur adapters, and Teflon PEEK tubing, the syringe is connected to the glass microchip. The flow rates are varied from 0 μL/min to 15 μL/min through the 200 μm-wide PDMS flow channel which is aligned with one end at the flow access hole. The channel is sealed directly over the electrode. At the other end of the channel, a reservoir is formed by a hole punch and is where the cathode or reference and counter electrodes are placed.

The carbon ink electrode generally is a 2.5 cm long electrode that is 55 μm wide and 87 μm high. A solution of 1 mM tris(2,2'-bipyridyl)dichlororuthenium(II) hexahydrate and 0.1M sodium sulfate as the electrolyte is used to characterize the response of the electrode using cyclic voltammetry. As flow rate is increased, the current density increased which is expected due to the analyte reaching the electrode surface faster with an increase in flow rates. Initially, an electrochemical pretreatment is utilized to clean the electrode by applying 1.5 V for 3 minutes in a 0.05 M phosphate buffer (pH 7.4).

The procedure above is followed with slight modification to simplify the process of forming an electrode comprising an electron conductor and an enzyme immobilization material. To do so, the electron conductor solution is modified to include the enzyme immobilization material. The additional material is prepared by adding a 2 wt. % solution of a hydrophobically modified chitosan in t-amyl alcohol or a 3 wt. % solution of hydrophobically modified alginate in alcohol is suspended in Ercon N160 Solvent Thinner and vortexed thoroughly. Finally, 1 mL of this modified thinner is added to 0.5 g Ercon E-978(1) carbon-based ink. This modified electron conductor solution is then flowed through the mold cavity formed by the casting mold and the substrate and cured according to the method described above in this example.

To form a bioanode according to the invention, the general steps above in this example are used, with the anode being completed by flowing additional materials over the electron conductor after its curing and activation stages. A casting solution of the remaining anode elements is created by combining a 2 wt. % solution of hydrophobically modified chitosan in t-amyl alcohol or a 3 wt. % solution of hydrophobically modified alginate in alcohol, and an enzyme solution in lower aliphatic alcohol. This solution is then vortexed together thoroughly and pumped through the approximately 100 mm microchannel at a flow rate of about 1 mL/min. The electron conductor and the casting solution are then allowed to dry overnight.

For the biocathode, the microchips and channel masters are fabricated as described above in this example using photolithography. The carbon ink microelectrodes generated from the micromolding procedure could be further modified with the hydrophobically modified chitosan or hydrophobically modified alginate membrane mixtures described above.

The carbon microelectrodes are modified to serve as a bioanode. A hole is punched in PDMS to form a bulk reservoir that is placed around the microelectrode and include Ag/AgCl reference electrode and a platinum wire as the auxiliary electrode. Specifically, this is a static cell.

The enzyme/hydrophobically modified chitosan mixture or enzyme/hydrophobically modified alginate mixture is immobilized onto the carbon microelectrode using microchannels that are reversibly sealed over the microelectrodes and hydrodynamic flow. The size of this flow channel is such that alignment over the microelectrode is possible but is not much wider than the electrode. To accomplish this, a PDMS microchannel (130 mm wide, 100 mm deep and ~2 cm long) is sealed over the carbon electrode (~40 mm wide, ~2 cm long, and ~100 mm high), so that the entire electrode is sealed inside the microchannel. A 2:1 ratio of enzyme and hydrophobically modified chitosan mixture or hydrophobically modified alginate mixture is prepared and vortexed until sufficiently mixed. The mixture is introduced to the channels thru a syringe by use of a syringe pump (Harvard Apparatus, Brookfield, Ohio) at 1.0 mL/min. Once the mixture travels the entire length of the channel (monitored visually), the solvent is allowed to evaporate at room temperature. This is possible since PDMS is permeable to gases. After evaporation is complete, the PDMS is removed, leaving a coated bioanode.

To form a biocathode according to the invention, the general steps described in this example are used, with the biocathode being completed by flowing additional materials over the electron conductor after its curing and activation stages.

To modify the electron conductor, a casting solution of bilirubin oxidase, and a hydrophobically modified chitosan or hydrophobically modified alginate is vortexed together for about 20 minutes. Next, the solution is pumped through the approximately 100 mm microchannel at a flow rate of about 1 mL/min. The electron conductor and the casting solution are then allowed to dry overnight.

The biocathode is created in a similar fashion to the bioanode described above. A PDMS microchannel is sealed over a carbon ink microelectrode. Hydrophobically modified chitosan is mixed with a cathode enzyme. The mixture is then pumped through the channel at a 1.0 mL/min until it reached the end of the channel after which time the solvent is allowed to evaporate. Afterwards the PDMS flow channel is removed leaving a coated electrode that is used as a biocathode.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

What is claimed is:

1. A bioanode consisting essentially of
    (a) an electron conductor;
    (b) at least one anode enzyme capable of reacting with a fuel fluid to produce an oxidized form of the fuel fluid, the anode enzyme being capable-of directly releasing electrons to the electron conductor; and
    (c) an enzyme immobilization material immobilizing and stabilizing the enzyme, the material being permeable to the fuel fluid;
    wherein the enzyme is stabilized when it retains at least about 75% of its initial catalytic activity upon continuous operation in a biofuel cell for at least about 7 days to about 730 days.

2. The bioanode of claim 1 wherein the enzyme immobilization material comprises a micellar or inverted micellar structure.

3. The bioanode of claim 1 wherein the enzyme immobilization material comprises either
(a) a modified perfluoro sulfonic acid-PTFE copolymer or a hydrophobically modified alginate wherein the enzyme immobilization material is modified with a hydrophobic cation larger than $NH_4^+$; or
(b) a hydrophobically modified polysaccharide.

4. The bioanode of claim 3 wherein the hydrophobic cation comprises a quaternary ammonium ion represented by Formula 4

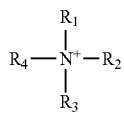

4 wherein $R_1$, $R_2$, $R_3$ and $R_4$ are independently hydrogen, hydrocarbyl, substituted hydrocarbyl or heterocyclo wherein at least one of $R_1$, $R_2$, $R_3$ and $R_4$ is other than hydrogen.

5. The bioanode of claim 3 wherein said hydrophobically modified polysaccharide corresponds to Formula 1

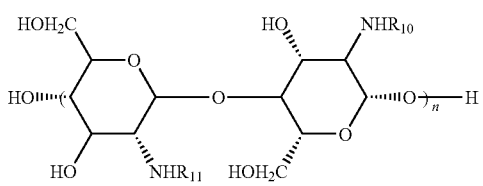

1 wherein n is an integer;
$R_{10}$ is independently hydrogen, hydrocarbyl, or substituted hydrocarbyl; and
$R_{11}$ is independently hydrogen, hydrocarbyl, or substituted hydrocarbyl.

6. The bioanode of claim 5 wherein $R_{10}$ is independently hydrogen or alkyl and $R_{11}$ is independently hydrogen or alkyl.

7. The bioanode of claim 1 wherein the electron conductor comprises carbon cloth, carbon paper, carbon screen printed electrodes, carbon black, carbon powder, carbon fiber, single-walled carbon nanotubes, double-walled carbon nanotubes, multi-walled carbon nanotubes, carbon nanotube arrays, diamond-coated conductors, glass carbon, mesoporous carbon, graphite, uncompressed graphite worms, delaminated purified flake graphite, high performance graphite, highly ordered pyrolytic graphite, pyrolytic graphite or polycrystalline graphite.

8. The bioanode of claim 1 wherein the anode enzyme comprises a PQQ-dependent dehydrogenase or a lipoxygenase.

9. A biocathode consisting essentially of:
(a) an electron conductor;
(b) at least one cathode enzyme capable of reacting with an oxidant to produce water, the cathode enzyme being capable of directly gaining electrons from the electron conductor; and
(c) an enzyme immobilization material immobilizing and stabilizing the enzyme, the material being permeable to the oxidant;
wherein the enzyme is stabilized when it retains at least about 75% of its initial catalytic activity upon continuous operation in a biofuel cell for at least about 7 days to about 730 days.

10. The biocathode of claim 9 wherein the enzyme immobilization material comprises a micellar or inverted micellar structure.

11. The biocathode of claims 9 wherein the enzyme immobilization material comprises either
(a) a modified perfluoro sulfonic acid-PTFE copolymer or a hydrophobically modified alginate wherein the enzyme immobilization material is modified with a hydrophobic cation larger than $NH_4^+$; or
(b) a hydrophobically modified polysaccharide.

12. The biocathode of claim 11 wherein the hydrophobic cation comprises a quaternary ammonium ion represented by Formula 4

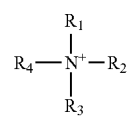

4 wherein $R_1$, $R_2$, $R_3$ and $R_4$ are independently hydrogen, hydrocarbyl, substituted hydrocarbyl or heterocyclo wherein at least one of $R_1$, $R_2$, $R_3$ and $R_4$ is other than hydrogen.

13. The biocathode of claim 11 wherein said hydrophobically modified polysaccharide corresponds to Formula 1

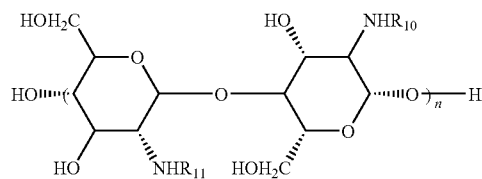

1 wherein n is an integer;
$R_{10}$ is independently hydrogen, hydrocarbyl, or substituted hydrocarbyl; and
$R_{11}$ is independently hydrogen, hydrocarbyl, or substituted hydrocarbyl.

14. The biocathode of claim 13 wherein $R_{10}$ is independently hydrogen or alkyl and $R_{11}$ is independently hydrogen or alkyl.

15. The biocathode of claim 9 wherein the electron conductor comprises carbon cloth, carbon paper, carbon screen printed electrodes, carbon black, carbon powder, carbon fiber, single-walled carbon nanotubes, double-walled carbon nanotubes, multi-walled carbon nanotubes, carbon nanotube arrays, diamond-coated conductors, glass carbon, mesoporous carbon, graphite, uncompressed graphite worms, delaminated purified flake graphite, high performance graphite, highly ordered pyrolytic graphite, pyrolytic graphite or polycrystalline graphite.

16. The biocathode of claim 9 wherein the cathode enzyme comprises bilirubin oxidase or superoxide dismutase.

17. A biofuel cell for generating electricity comprising:
a fuel fluid;
a bioanode of claim 1; and
a cathode.

18. A biofuel cell for generating electricity comprising:
a fuel fluid;
an anode; and
a biocathode of claim 9.

19. The biofuel cell of claim 17 wherein the cathode comprises a biocathode of claim 9.

20. The biofuel cell of claim 18 wherein the oxidant comprises oxygen or peroxide.

21. The biofuel cell of claim 17 wherein the fuel fluid comprises ammonia, methanol, ethanol, propanol, isobutanol, butanol, isopropanol, an allyl alcohol, an aryl alcohol, glycerol, propanediol, mannitol, glucuronate, aldehyde, a carbohydrate, glucose, glucose-1, D-glucose, L-glucose, glucose-6-phosphate, lactate, lactate-6-phosphate, D-lactate, L-lactate, fructose, galactose-1, galactose, aldose, sorbose, mannose, glycerate, coenzyme A, acetyl Co-A, malate, isocitrate, formaldehyde, acetaldehyde, acetate, citrate, L-gluconate, beta-hydroxysteroid, alpha-hydroxysteroid, lactaldehyde, testosterone, gluconate, a fatty acid, a lipid, phosphoglycerate, retinal, estradiol, cyclopentanol, hexadecanol, a long-chain alcohol, coniferyl-alcohol, cinnamyl-alcohol, formate, a long-chain aldehyde, pyruvate, butanal, acyl-CoA, a steroid, an amino acid, flavin, NADH, $NADH_2$, NADPH, $NADPH_2$ or hydrogen.

22. A bioanode comprising
 (a) an electron conductor;
 (b) at least one anode enzyme capable of reacting with a fuel fluid to produce an oxidized form of the fuel fluid, the anode enzyme capable of directly releasing electrons to the electron conductor; and
 (c) an enzyme immobilization material immobilizing and stabilizing the enzyme, the material being permeable to the fuel fluid;
 wherein the enzyme is stabilized when it retains at least about 75% of its initial catalytic activity upon continuous operation in a biofuel cell for at least about 7 days to about 730 days and the bioanode does not contain an electron mediator.

23. The bioanode of claim 22 wherein the anode enzyme comprises more than one redox center.

24. The bioanode of claim 23 wherein the anode enzyme comprises a PQQ-dependent dehydrogenase or a lipoxygenase.

25. A biocathode comprising:
 (a) an electron conductor;
 (b) at least one cathode enzyme capable of reacting with an oxidant to produce water, the cathode enzyme being capable of directly gaining electrons from the electron conductor; and
 (c) an enzyme immobilization material immobilizing and stabilizing the enzyme, the material being permeable to the oxidant;
 wherein the enzyme is stabilized when it retains at least about 75% of its initial catalytic activity upon continuous operation in a biofuel cell for at least about 7 days to about 730 days and the biocathode does not contain an electron mediator.

26. The biocathode of claim 25 wherein the cathode enzyme comprises more than one redox center.

27. The biocathode of claim 26 wherein the cathode enzyme comprises bilirubin oxidase or superoxide dismutase.

28. The bioanode of claim 1 wherein the anode enzyme comprises more than one redox center.

29. The biocathode of claim 9 wherein the cathode enzyme comprises more than one redox center.

* * * * *